United States Patent [19]

Wegner et al.

[11] Patent Number: 5,324,510
[45] Date of Patent: Jun. 28, 1994

[54] USE OF ANTIBODIES TO INTERCELLULAR ADHESION MOLECULE-1 (ICAM-1) IN THE TREATMENT OF ASTHMA

[75] Inventors: Craig D. Wegner, New Milford, Conn.; Robert H. Gundel, Pawling, N.Y.; Robert Rothlein, Danbury, Conn.

[73] Assignee: Boehringer Ingelheim Pharmaceuticals, Inc., Ridgefield, Conn.

[21] Appl. No.: 37,461

[22] Filed: Mar. 18, 1993

Related U.S. Application Data

[63] Continuation of Ser. No. 401,409, Sep. 1, 1989, abandoned.

[51] Int. Cl.$^5$ .................. A61K 39/00; A61K 39/395; C02K 15/28
[52] U.S. Cl. .............................. 424/85.8; 530/388.22; 530/388.7; 530/388.85; 530/389.6; 530/866; 530/868
[58] Field of Search .................. 424/85.8; 530/388.22, 530/388.7, 388.85, 389.6, 868, 866

[56] References Cited

U.S. PATENT DOCUMENTS

| | | | |
|---|---|---|---|
| 5,011,778 | 4/1991 | Newman et al. | 435/240.27 |
| 5,202,116 | 4/1993 | Brown et al. | 424/85.1 |
| 5,223,396 | 6/1993 | Rothlein et al. | 435/7.21 |
| 5,235,049 | 10/1993 | McClelland et al. | 435/240.2 |

OTHER PUBLICATIONS

*Basic and Clinical Immunol.* (1980). Fudenberg, et al. (ed.) Lange med. Pub. Los Altos CA pp. 2545.
Rothlein, R. et al. *J. Immunol.* 137:1270–4 (1986). "A Human Intracell. Adh. Mol. (ICAM-1) . . . ".
Dustin, M. L. et al. *J. Immunol.* (1986). vol. 137 (I), pp. 245–254. "Induction by IL–1 and . . . ".
Frigas, E. et al., *J. Allergy Clin. Immunol.* 77(4):527–537 (1986).
De Monchy, J. G. R. et al., *Am. Rev. Respir. Dis.* 131:373–376 (1985).
Smith, C. W. et al., *J. Clin. Invest.* 82:1746–1756 (1988).
Wegner, C. D. et al., *Am. Rev. Respir. Dis.* 139:A342 (1989).
Vejlsgaard, G. L. et al., *J. Am. Acad. Dermatol.* 20(5):782–790 (1989).
Wegner, C. D. et al., *Science* 247:456–459 (1990).

*Primary Examiner*—Christine M. Nucker
*Assistant Examiner*—Thomas M. Cunningham
*Attorney, Agent, or Firm*—Sterne, Kessler, Goldstein & Fox

[57] ABSTRACT

The present invention provides a method of reducing the severity of asthma. Specifically, the present invention discloses that anti-adhesion antibodies, such as anti-ICAM-1 or anti-CD18 family member antibodies, when administered to a mammal, are capable of decreasing the hyperresponsive reaction associated with an asthmatic response.

4 Claims, 12 Drawing Sheets

5' GCGCCCCAGTCGACGCTGAGCTCCTCTGCTACTCAGAGTTGCAACCTCAGCCTCGCT    57

```
ATG GCT CCC AGC AGC CCC CGG CCC GCG CTG CCC GCA CTC CTG GTC
 M   A   P   S   S   P   R   P   A   L   P   A   L   L   V
```

```
CTG CTC GGG GCT CTG TTC CCA GGA CCT GGC AAT GCC CAG ACA TCT    147
 L   L   G   A   L   F   P   G   P   G   N   A   Q   T   S      3
```

```
GTG TCC CCC TCA AAA GTC ATC CTG CCC CGG GGA GGC TCC GTG CTG
 V   S   P   S   K   V   I   L   P   R   G   G   S   V   L
```

```
GTG ACA TGC AGC ACC TCC TGT GAC CAG CCC AAG TTG TTG GGC ATA    237
 V   T   C   S   T   S   C   D   Q   P   K   L   L   G   I     33
```

```
GAG ACC CCG TTG CCT AAA AAG GAG TTG CTC CTG CCT GGG AAC AAC
 E   T   P   L   P   K   K   E   L   L   L   P   G   N   N
```

```
CGG AAG GTG TAT GAA CTG AGC AAT GTG CAA GAA GAT AGC CAA CCA    327
 R   K   V   Y   E   L   S   N   V   Q   E   D   S   Q   P     63
```

```
ATG TGC TAT TCA AAC TGC CCT GAT GGG CAG TCA ACA GCT AAA ACC
 M   C   Y   S   N   C   P   D   G   Q   S   T   A   K   T
```

```
TTC CTC ACC GTG TAC TGG ACT CCA GAA CGG GTG GAA CTG GCA CCC    417
 F   L   T   V   Y   W   T   P   E   R   V   E   L   A   P     93
```

```
CTC CCC TCT TGG CAG CCA GTG GGC AAG AAC CTT ACC CTA CGC TGC
 L   P   S   W   Q   P   V   G   K  [N   L   T]  L   R   C
```

```
CAG GTG GAG GGT GGG GCA CCC CGG GCC AAC CTC ACC GTG GTG CTG    507
 Q   V   E   G   G   A   P   R   A  [N   L   T]  V   V   L    123
```

```
CTC CGT GGG GAG AAG GAG CTG AAA CGG GAG CCA GCT GTG GGG GAG
 L   R   G   E   K   E   L   K   R   E   P   A   V   G   E
```

```
CCC GCT GAG GTC ACG ACC ACG GTG CTG GTG AGG AGA GAT CAC CAT    597
 P   A   E   V   T   T   T   V   L   V   R   R   D   H   H    153
```

```
GGA GCC AAT TTT TCG TGC CGC ACT GAA CTG GAC CTG CGG CCC CAA
 G   A  [N   F   S]  C   R   T   E   L   D   L   R   P   Q
```

```
GGG CTG GAG CTG TTT GAG AAC ACC TCG GCC CCC TAC CAG CTC CAG    687
 G   L   E   L   F   E  [N   T   S]  A   P   Y   Q   L   Q    183
```

```
ACC TTT GTC CTG CCA GCG ACT CCC CCA CAA CTT GTC ACC CCC CCG
 T   F   V   L   P   A   T   P   P   Q   L   V   S   P   R
```

```
GTC CTA GAG GTG GAC ACG CAG GGG ACC GTG GTC TGT TCC CTG GAC    777
 V   L   E   V   D   T   Q   G   T   V   V   C   S   L   D    213
```

FIG. 1a

```
GGG CTG TTC CCA GTC TCG GAG GCC CAG GTC CAC CTG GCA CTG GGG
 G   L   F   P   V   S   E   A   Q   V   H   L   A   L   G

GAC CAG AGG TTG AAC CCC ACA GTC ACC TAT GGC AAC GAC TCC TTC     867
 D   Q   R   L   N   P   T   V   T   Y   G  [N   Q   S]  F     243

TCG GCC AAG GCC TCA GTC AGT GTG ACC CGA GAG GAC GAG GGC ACC
 S   A   K   A   S   V   S   V   T   A   E   D   E   G   T

CAG CGG CTG ACG TGT GCA GTA ATA CTG GGG AAC CAG AGC CAG GAG     957
 Q   R   L   T   C   A   V   I   L   G  [N   Q   S]  Q   E     273

ACA CTG CAG ACA GTG ACC ATC TAC AGC TTT CCG GCG CCC AAC GTG
 T   L   Q   T   V   T   I   Y   S   F   P   A   P   N   V

ATT CTG ACG AAG CCA GAG GTC TCA GAA GGG ACC GAG GTG ACA TGT    1047
 I   L   T   K   P   E   V   S   E   G   T   E   V   T   V     303

AAG TGT GAG GCC CAC CCT AGA GCC AAG GTG ACG CTG AAT GGG GTT
 K   C   E   A   H   P   R   A   K   V   T   L   N   G   V

CCA CCC CAG CCA CTG GGC CCG AGG GCC CAG CTC CTG CTG AAG GCC    1137'
 P   A   Q   P   L   G   P   R   A   Q   L   L   L   K   S     333

ACC CCA GAG GAC AAC GGG CGC AGC TTC TCC TGC TCT GCA ACC CTG
 T   P   E   D   N   G   R   S   F   S   C   S   A   T   L

GAG GTG GCC GGC CAG CTT ATA CAC AAG AAG CAG ACC CGG GAG CTT    1227
 E   V   A   G   Q   L   I   H   K  [N   Q   T]  R   E   L     363

CGT GTC CTG TAT GGC CCC CGA CTG GAC GAG AGG GAT GTG CCG GGA
 R   V   L   Y   G   P   R   L   D   E   R   D   C   P   G

AAC TGG ACG TGG CCA GAA AAT TCC CAG CAG ACT CCA ATG TGC CAG    1317
[N   W   T]  W   P   E   N   S   Q   Q   T   P   M   C   Q     393

GCT TGG GGG AAC CCA TTG CCC GAG CTC AAG TGT CTA AAG GAT GGC
 A   W   G   N   P   L   P   E   L   K   C   L   K   D   G

ACT TTC CCT CTG CCC ATC GGG GAA TCA GTG ACT GTC ACT CGA GAT    1407
 T   F   P   L   P   I   G   E   S   V   T   V   T   R   D     423

CTT GAG GGC ACC TAC CTC TGT CGG GCC AGG AGC ACT CAA GGG GAG
 L   E   G   T   Y   L   C   R   A   R   S   T   Q   G   E

GTC ACC CGC GAG GTG ACC GTG AAT GTG CTC TCC CCC CGG TAT GAG    1497
 V   T   R   E   V   T   V   N   V   L   S   P   R   Y   E     453

ATT GTC ATC ATC ACT GTG GTA GCA GCC GCA GTC ATA ATG GGC ACT
 I   V   I   I   T   V   V   A   A   A   V   I   M   G   T
```

FIG. 1b

```
GCA GGC CTC AGC ACG TAC CTC TAT AAC CGC CAG CGG AAG ATC AAG   1587
 A   G   L   S   T   Y   L   Y   N   R   Q   R   K   I   K    483

AAA TAC AGA CTA CAA CAG GCC CAA AAA GGG ACC CCC ATG AAA CCG
 K   Y   R   L   Q   Q   A   Q   K   G   T   P   M   K   P

AAC ACA CAA GCC ACG CCT CCC TGA ACCTATCCCGGGACAGGGCCTCTTCCT   1683
 N   T   Q   A   T   P   P   *                                505

CGGCCTTCCCATATTGGTGGCAGTGGTGCCACACTGAACAGAGTGGAAGACATATGCCA
TGCAGCTACACCTACCGGCCCTGGGACGCCGGAGGACAGGGCATTGTCCTCATTCAGATA  1802

CAACAGCATTTGGGGCCATGGTACCTGCACACCTAAAACACTAGGCCACGCATCTGATC
TGTAGTCACATGACTAAGCCAAGAGGAAGGAGCAAGACTCAAGACATGATGACTGGATGT  1921

TAAAGTCTAGCCTGATGAGAGGGGAAGTGGTGGGGGAGACATAGCCCCACCATGACGAC
ATACAACTGGGAAATACTGAAACTTGCTCCCTATTGGGTATGCTGAGGCCCACAGACTTA  2040

CAGAAGAAGTGGCCCTCCATAGACATGTGTAGCATCAAAACACAAAGGCCCACACTTCC
TGACGGATGCCAGCTTGGGCACTGCTGTCTACTGACCCCAACCCTTGATGATATGTATTT  2159

ATTCATTTGTTATTTTACCAGCTATTTATTGAGTGTCTTTTATGTAGCCTAAATGAACA
TAGGTCTCTGGCCTCACGGAGCTCCCAGTCCATGTCACATTCAAGGTCACCAGGTACAGT  2278

TGTACAGGTTGTACACTGCAGGAGAGTGCCTGGCAAAAAGATCAAATGGGGCTGGGACT
TCTCATTGGCCAACCTGCCTTTCCCCAGAAGGAGTGATTTTTCTATCGGCACAAAAGCAT  2397

TATATGGACTGGTAATGGTTCACAGGTTCAGAGATTACCCAGTGAGGCCTTATTCCTCC
CTTCCCCCCAAAACTGACACCTTTGTTAGCCACCTCCCCACCCACATACATTTCTGCCAG  2516

TGTTCACAATGACACTCAGCGGTCATGTCTGGACATGAGTGCCCAGGGAATATGCCCAA
GCTATGCCTTGTCCTCTTGTCCTGTTTGCATTTCACTGGGAGTTTGCATTATTCCAGCTC  2635

CAGTTTCCTGCAGTGACTCAGGGTCCTGCAAGCAGTGGGGAAGGGGGCCAAGGTATGGA
GGACTCCCTCCCAGCTTTGGAAGGGTCATCCCCGTGTGTGTGTGTGTATGTGTAGACA    2754

AGCTCTCGCTCTGTCACCCAGGCTGGAGTGCAGTGGTGCAATCATGGTTCACTGCAGTC
TTGACCTTTTGGGCTCAAGTGATCCTCCCACCTCAGCCTCCTGAGTAGCTGGGACCATAG  2873

GCTCACAACACCACACCTGGCAAATTTGATTTTTTTTTTTTTTTTCAGAGACGGGGTCT
CGCAACATTGCCCAGACTTCCTTTGTGTTACTTAATAAAGCTTTCTCAACTGCCAAAAAA  2992

AAAAAAAAAAAAAAAAAAAAAAAAAAAAA 3'     FIG. 1c
```

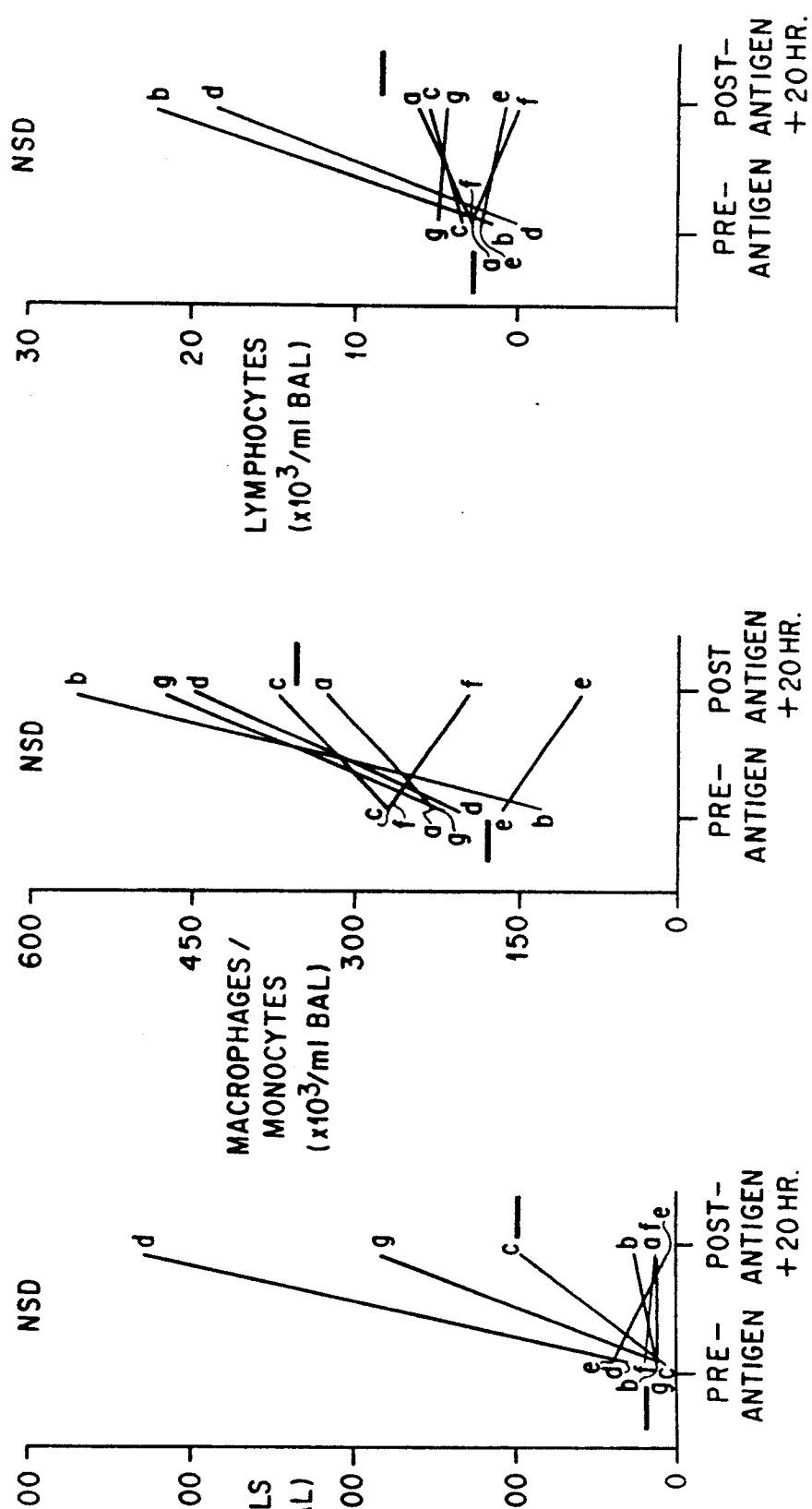

USE OF ANTIBODIES TO INTERCELLULAR ADHESION MOLECULE-1 (ICAM-1) IN THE TREATMENT OF ASTHMA

This application is a continuation of U.S. Ser. No. 07/401,409, filed Sep. 1, 1989.

FIELD OF THE INVENTION

The present invention relates to the use of intercellular adhesion molecules such as ICAM-1 in the treatment of asthma. The invention additionally concerns ligand molecules capable of binding to such intercellular adhesion molecules, and to an assay for detecting agents having therapeutic potential in the treatment of asthma.

DESCRIPTION OF THE RELATED ART

A. Cellular Adhesion

Leukocytes must be able to attach to cellular substrates in order to properly defend the host against foreign invaders such as bacteria or viruses. An excellent review of the defense system is provided by Eisen, H. W., (In: *Microbiology*, 3rd Ed., Harper & Row, Philadelphia, Pa. (1980), pp. 290-295 and 381-418). Leukocytes must be able to attach to endothelial cells so that they can migrate from circulation to sites of ongoing inflammation. Furthermore, they must attach to antigen-presenting cells so that a normal specific immune response can occur, and finally, they must attach to appropriate target cells so that lysis of virally-infected or tumor cells can occur.

Leukocyte surface molecules involved in mediating such attachments have been identified using hybridoma technology. Briefly, monoclonal antibodies ("MAbs") directed against human T-cells (Davignon, D. et al., *Proc. Natl. Acad. Sci. U.S.A.* 78:4535-3539 (1981)) and mouse spleen cells (Springer, T. et al., *Eur. J. Immunol.* 9:301-306 (1979)) were identified which bound to leukocyte surfaces and inhibited the attachment related functions described above (Springer, T. et al., *Fed. Proc.* 44:2660-2663 (1985)). The molecules identified by those antibodies were called Mac-1 and Lymphocyte Function-associated Antigen-1 (LFA-1). Mac-1 is found on macrophages, granulocytes and large granular lymphocytes. LFA-1 is found on most lymphocytes (Springer, T. A., et al. *Immunol. Rev.* 68:111-135 (1982)). These two molecules, plus a third molecule, p150,95 (which has a tissue distribution similar to Mac-1) play a role in cellular adhesion (Keizer, G. et al., *Eur. J. Immunol.* 15:1142-1147 (1985)). Molecules such as those of LFA-1 family, which are involved in the process of cellular adhesion are referred to as "adhesion molecules."

The above-described leukocyte molecules were found to be structurally similar to one another, and to constitute members of a related family of glycoproteins (Sanchez-Madrid, F. et al., *J. Exper. Med.* 158:1785-1803 (1983); Keizer, G. D. et al., *Eur. J. Immunol.* 15:1142-1147 (1985)). This glycoprotein family is composed of heterodimers having one alpha subunit and one beta subunit. Although the alpha subunit of each of the antigens differed from one another, the beta subunit was found to be highly conserved (Sanchez-Madrid, F. et al., *J. Exper. Med.* 158:1785-1803 (1983)). The beta subunit of the glycoprotein family (referred to as "CD18" family) was found to have a molecular weight of 95 kd whereas the alpha subunits were found to vary from 150 kd to 180 kd (Springer, T., *Fed. Proc.* 44:2660-2663 (1985)). Although the alpha subunits of the membrane proteins do not share the extensive homology shared by the beta subunits, close analysis of the alpha subunits of the glycoproteins has revealed that there are substantial similarities between them. Reviews of the similarities between the alpha and beta subunits of the LFA-1 related glycoproteins are provided by Sanchez-Madrid, F. et al., (*J. Exper. Med.* 158:586-602 (1983); *J. Exper. Med.* 158:1785-1803 (1983)).

A group of individuals has been identified who are unable to express normal amounts of any member of this adhesion protein family on their leukocyte cell surface (Anderson, D. C., et al., *Fed. Proc.* 44:2671-2677 (1985); Anderson, D. C., et al., *J. Infect. Dis.* 152:668-689 (1985)). The condition is known as "Leukocyte Adhesion Deficiency" or "LAD" syndrome. Leukocytes from these patients displayed in vitro defects similar to normal counterparts whose CD18 family of molecules had been antagonized by antibodies. Furthermore, these individuals are unable to mount a normal immune response due to an inability of their cells to adhere to cellular substrates (Anderson, D. C., et al., *Fed. Proc.* 44:2671-2677 (1985); Anderson, D. C., et al., *J. Infect. Dis.* 152:668-689 (1985)). LAD individuals present clinically with delayed umbilical cord separation, recurring and progressive soft tissue infections, and impaired pus formation, despite a striking blood leukocytosis. Studies of LAD individuals have revealed that immune reactions are mitigated when lymphocytes are unable to adhere in a normal fashion due to the lack of functional adhesion molecules of the CD18 family.

Thus, in summary, the ability of leukocytes, especially lymphocytes to maintain the health and viability of an animal requires that they be capable of adhering to other cells (such as endothelial cells). This adherence has been found to require cell-cell contacts which involve specific receptor molecules present on the cell surface of the lymphocytes. These receptors enable a lymphocyte to adhere to other lymphocytes or to endothelial, and other non-vascular cells. The cell surface receptor molecules have been found to be highly related to one another. Humans whose lymphocytes lack these cell surface receptor molecules exhibit defective antibody responses, chronic and recurring infections, as well as other clinical symptoms.

B. Asthma: Clinical Characteristics

Asthma is a heterogeneous family of diseases. It is characterized by a hyper-responsiveness of the tracheobronchi to stimuli (McFadden, E. R. et al., In: *Harrison's Principles of Internal Medicine*, 10th Ed., Petersdorf, R. G. et al., Eds., McGraw-Hill, N.Y. (1983), pages 1512- 1519); Kay, A. G., *Allergy and Inflammation*, Academic Press, N.Y. (1987); which references are incorporated herein by reference). Clinically, asthma is manifested by the extensive narrowing of the tracheobronchi, by thick tenacious secretions, by paroxysms of dyspnea, cough, and wheezing. Although the relative contribution of each of these conditions is unknown, the net result is an increase in airway resistance, hyperinflation of the lungs and thorax, abnormal distribution of ventilation and pulmonary blood flow. The disease is manifested in episodic periods of acute symptoms interspersed between symptom-free periods. The acute episodes result in hypoxia, and can be fatal. Approximately 3% of the general world population suffers from the disease.

Two types of asthma have been described: allergic asthma and idiosyncratic asthma. Allergic asthma is usually associated with a heritable allergic disease, such as rhinitis, urticaria, eczema, etc. The condition is characterized by positive wheal-and-flare reactions to intradermal injections of airborne antigens (such as pollen, environmental or occupational pollutants, etc.), and increased serum levels of IgE. The development of allergic asthma appears to be causally related to the presence of IgE antibodies in many patients. Asthma patients who do not exhibit the above-described characteristics are considered to have idiosyncratic asthma.

Allergic asthma is believed to be dependent upon an IgE response controlled by T and B lymphocytes and activated by the interaction of airborne antigen with mast cell-bound pre-formed IgE molecules. The antigenic encounter must have occurred at concentrations sufficient to lead to IgE production for a prolonged period of time in order to sensitize an individual. Once sensitized, an asthma patient may exhibit symptoms in response to extremely low levels of antigen.

Asthma symptoms may be exacerbated by the presence and level of the triggering antigen, environmental factors, occupational factors, physical exertion, and emotional stress.

Asthma may be treated with methylxanthines (such as theophylline), beta-adrenergic agonists (such as catecholamines, resorcinols, saligenins, and ephedrine), glucocorticoids (such as hydrocortisone), inhibitors of mast cell degranulation (i.e. chromones such as cromolyn sodium) and anticholinergics (such as stropine).

C. Asthma: Immunological Characteristics

Asthma is believed to involve an influx of eosinophils ("eosinophilia") into the tissues of the lung (Frigas, E. et al., *J. Allergy Clin. Immonol.* 77:527–537 (1986), which reference is incorporated herein by reference). Eosinophils contain an arginine-rich, strongly basic protein which has been termed "MBP" (Gleich, G. J. et al., *J. Exper. Med.* 137:1459 (1973)). MBP comprises more than 50% of the granule protein of the eosinophil.

MBP was found to be toxic to normal mammalian cells, and to be expressed at toxic levels in tissues evidencing eosinophilia, such as the lung tissue of asthma patients (Gleich, G. J. et al., *J. Immunol.* 123:2925 (1975). The linkage between MBP expression and asthma was strengthened by the discovery that the MBP levels found in the sputum of asthma patients was elevated relative to normal individuals (Frigas, E. et al., *Mayo Clin. Proc.* 56:345 (1981)). Since the discovery of MBP, other cytotoxic eosinophil proteins have been identified (Frigas, E. et al., *J. Allergy Clin. Immunol.* 77:527–537 (1986)).

Insight into the immunological basis of asthma has been gained from the above-described studies, from bronchoalveolar lavage studies (Godard, P. et al., *J. Allergy Clin. Immunol.* 70:88 (1982)), and studies of repiratory smooth muscle denuded of epithelium (Flavahan, N. A. et al., *J. Appl. Physiol.* 58:834 (1985); Barnes, P. J. et al., *Br. J. Pharmacol.* 86:685 (1985)). Although these studies have not led to the elucidation of the mechanism underlying the immunology of asthma, they have led to the development of a generally accepted hypothesis concerning the immunological etiology of the disease (see, Frigas, E. et al., *J. Allergy Clin. Immunol.* 77:527–537 (1986)).

The hallmarks of the pathology of asthma are a massive infiltration of the lung parenchyma by eosinophils and the destruction f mucociliary capacity. The "eosinophil hypothesis" suggests that eisonophils are attracted to the bronchus in order to neutralize harmful mediators released by the mast cells of the lung. According to the hypothesis eosinophils are attracted to the bronchi where they degranulate to release MBP and other cytotoxic molecules. Upon degranulation, eosinophils release enzymes such as histaminase, arylsulfatase and phospholipase D which enzymatically neutralize the harmful mediators of the amst cell. These molecules also promote the destruction of the mucociliary apparatus, and thus prevent the clearing of the bronchial secretions, and contribute to the lung damage characteristic of asthma.

Thus, it is believed that asthma is caused by the eosinophils which invade the bronchi in an abnormal response to primary effects of antigen presence. The MBP of the eosinophils damage the epithelial cells of the bronchi. Leukotrienes and Platelet Activating Factor ("PAF") are produced by the eosinophil, and result in bronchial dilation. Molecules (such as MBP) released by the eosinophil can also activate mast cells to release leukotrienes and histamine, thereby causing both bronshospasm and increased eosinophilia.

In view of the clinical importance of asthma, it is highly desirable to identify new or improved therapies for treating asthma patients.

SUMMARY OF THE INVENTION

The present invention relates to the use of intercellular adhesion molecules ("ICAMs"), such as ICAM-1, and the functional derivatives of such ICAMs in the treatment of asthma. The invention further concerns the use of molecules (such as antibodies, or antibody fragments, or receptor molecules) that are able to bind to an intercellular adhesion molecule (or a derivative of an ICAM molecule) in the treatment of asthma. The invention also includes an assay for detecting agents having therapeutic potential in the treatment of asthma.

The invention additionally pertains to a method for treating asthma in a patient which comprises providing to the patient an effective therapeutic amount of an agent selected from the group consisting of:
  (a) an antibody capable of binding to ICAM-1;
  (b) a fragment of the antibody (a), the fragment being capable of binding to ICAM-1;
  (c) ICAM-1, being substantially free of natural contaminants;
  (d) a functional derivative of ICAM-1;
  (e) an antibody capable of binding to a member of the CD18 family of glycoproteins;
  (f) a fragment of the antibody (e), the fragment being capable of binding to a member of the CD18 family of glycoproteins;
  (g) a member of the CD18 family of glycoproteins, being substantially free of natural contaminants; and
  (h) a functional derivative of a member of the CD18 family of glycoproteins.

The invention further provides a method of identifying an agent capable of therapeutic potential in the treatment of asthma which comprises administering the agent to a non-human mammal (especially a primate) having received multiple inhalations of an antigen and then measuring any increase in airway responsiveness.

BRIEF DESCRIPTION OF THE FIGURES

FIG. 1, panels a, b and c show the nucleotide and amino acid sequence of ICAM-1 cDNA. The first ATG is at position 58. Translated sequences corresponding to ICAM-1 tryptic peptides are underlined. The hydrophobic putative signal peptide and transmembrane sequences have a bold underline. N-linked glycosylation sites are boxed. The polyadenylation signal AATAAA at position 2976 is over-lined. The sequence shown is for the HL-60 cDNA clone. The endothelial cell cDNA was sequenced over most of its length and showed only minor differences.

DESCRIPTION OF THE PREFERRED EMBODIMENTS

A. The Immunopathology of Asthma

Figure 2:
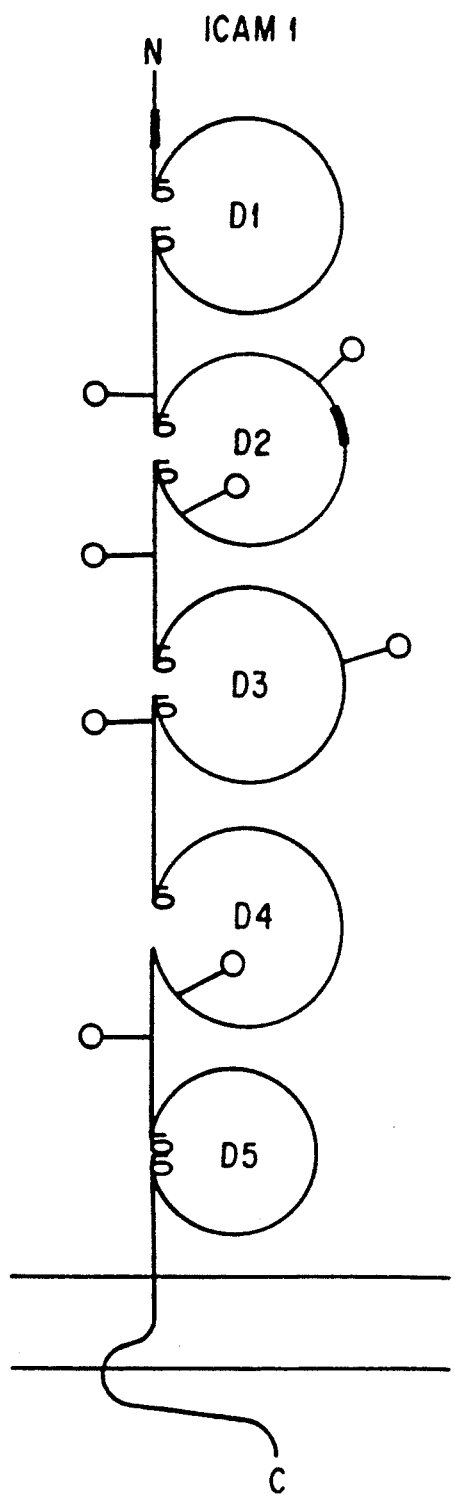
FIG. 2 shows the domain structure of ICAM-1.

As indicated above, one of the most important and characteristic features of asthma is the extreme (10 to 1000 times normal) sensitivity of the bronchi to inhaled agents (physical, chemical and physiological) (Boushey, H. A. et al., *Am. Rev. Respir. Dis.* 121:389 (1980); Hargreave, F. E. et al., *J. Allergy Clin. Immunol.* 68:347 (1981)).

The severity of this "airway hyperresponsiveness" (which is measured clinically by determining the responsiveness of the airways to inhaled histamine, methacholine, cold air or to exercise) correlates with the intensity of asthmatic symptoms (Hargreave, F. E. et al., *J. Allergy Clin. Immunol.* 68:347 (1981); Boulet, L-P et al., *J. Allergy Clin. Immunol.* 71:399 (1983); Chan-Yeung, M. et al., *Am. J. Med.* 72:411 (1982)), diurnal variations in peak flow rates (Ryan G. et al., *Thorax* 37:423 (1982)) and therapy required (Hargreave, F. E. et al., *J. Allergy Clin. Immunol.* 68:347 (1981); Juniper, E. F. et al., pi Thorax 36:575 (1981)).

Although airway hyperresponsiveness in asthmatics can remain stable over several years (Juniper E. G. et al., *Thorax* 37:288-291 (1982)), responsiveness has been shown to be increased by exposure to allergens (Boulet L.-P. et al., *J. Allergy, Clin. Immunol.* 71:399-177 (1982), Cockcroft D. W. et al., *Clinical Allergy* 7:503-513 (1977), Gundel R. H. et al., *Amer. Rev. Respir. Dis.* (1989), Lanes S. et al., *J. Appl. Physiol.* 61:864-872 (1986), Marsh W. R. et al., *Amer. Rev. Respir. Dis.* 131:875-879 (1985), Sotomayor H. et al., *Amer. Rev. Respir. Dis.* 130:56-58 (1984)), air pollutants (Golden J. A. et al., *Amer. Rev. Respir. Dis.* 113:131-139 (1976)) and certain occupational d chemicals (Chan-Yeung M. et al., *Amer. J. Med.* 72:411-415 (1982), Durham S. R. et al., *J. Allergy Clin. Immunol.* 79:398-306 (1987), Lam S. et al., *J. Allergy Clin. Immunol.* 72:134-139 (1983), Lam S. et al., *J. Clin. Immunol.* 63:28-34 (1979)). In fact, there is evidence to suggest that airway hyperresponsiveness is a consequence rather that a predisposing factor of asthma (Boulet L.-P. et al., *J. Allergy Clin Immunol.* 71:399-306 (1983), Chan-Yeung M. et al., *Amer J. Med.* 72:411-415 (1982), Gunder R. H. et al., *Amer. Rev. Respir. Dis.* (1989), Marsh W. R. et al., *Amer. Rev. Respir. Dis.* 131:875-879 (1985), Empey D. W. et al., *Amer. Rev. Respir. Dis.* 113:131-139 (1976), Lam S. et al., *J. Allergy Clin. Immunol.* 63:28-34 (1979)).

While the mechanisms underlying the pathogenesis of airway hyperresponsiveness are not known, results from many studies suggest, as indicated above, that eosinophil infiltration and desquamation of the bronchial epithelium are involved (DeMonchy, J. G. R. et al., *Am. Rev. Respir. Dis.* 131:373 (1985); Laitinen, L. A. et al., *Am. Rev. Respir. Dis.* 137:62 (1988)). Since eosinophil mediators have been shown to damage airway epithelial cells in vitro these two events may be linked (Frigas, E. et al., *J. allergy Clin. Immunol.* 77:527 (1986)).

B. Asthma and Intercellular Adhesion

The present invention derives, in part, from the development of an assay capable of identifying agents having therapeutic potential in the treatment of asthma.

As used herein, "asthma" refers to either allergic or idiosyncratic asthma. An agent is said to have a therapeutic potential in the treatment of asthma if it may lessen (i.e. attenuate) the severity, extent or duration of the asthma symptoms. Such agents are preferably identified through the use of the following "asthma model system". As used herein, an agent is said to be able to treat asthma if, when administered to a patient, the agent is capable of attenuating either the severity, extent or duration of the asthma symptoms.

One aspect of the present invention derives from the discovery that the migration of eosinophils into the lung is dependent upon intercellular adhesion, and specifically that such adhesion is dependent upon an "ICAM-1" ("Intercellular Adhesion Molecule-1") interaction.

As used herein, a molecule is a member of the CD18 family of glycoproteins is it contains either an alpha subunit of a member of the CD18 family of glycoproteins (i.e. a CD11 subunit), a beta subunit of a member of the CD18 family of glycoproteins (i.e. a CD18 beta subunit), or both an alpha and a beta subunit of a member of the CD18 family of glycoproteins. Thus, as used herein, a member of the CD18 family of glycoproteins includes molecules having only one subunit of a CD18 member as well as heterodimer (i.e. a molecule having both an alpha and a beta subunit of a member of the CD18 family. All such molecules may be either bound to a membrane or solid support or unbound (i.e. "soluble").

"ICAM-1" is the natural ligand for the CD18 family of glycoprotein receptor molecules (Rothlein, R. et al., *J. Immunol.* 137:1270 (1986); Marlin, S. D. et al., *Cell* 51:813 (1987)). ICAM-1 is a 76-97 kd glycoprotein. ICAM-1 is not a heterodimer. The identification, characterization, and amino acid sequence of ICAM-1, and the production of antibody reactive with ICAM-1 and other adhesion molecules are disclosed in European Patent Application Serial No. 289,949 (which reference is incorporated herein by reference) and in Rothlein, R. et al. (*J. Immunol.* 137:1270-1274 (1986)), Smith, C. W. et al., in *Structure and Function of Molecules Involved in Leukocyte Adhesion,* A. S. Rosenthal, et al., Eds. (Springer-Verlag, New York, 1989); Smith, C. W. et al., *J. Clin Invest.* 82:1746 (1988) and Barton, R. W. et al., *J. Immunol.* 143, (1989)), all of which reference are incorporated herein by reference).

In brief, ICAM-1 is a cell surface glycoprotein expressed on non-hematopoietic cells such as vascular endothelial cells, thymic epithelial cells, certain other epithelial cells, and fibroblasts, and on hematopoietic cells such as tissue macrophages, mitogen-stimulated T lymphocyte blasts, and germinal centered B cells and dendritic cells in tonsils, lymph nodes, and Peyer's patches. ICAM-1 is highly expressed on vascular endothelial cells in T cell areas in lymph nodes and tonsils showing reactive hyperplasia. ICAM-1 is expressed in low amounts on peripheral blood lymphocytes. ICAM-1 appears to be required for neutrophil migration into inflamed tissues. Phorbol ester-stimulated differentiation of some myelomonocytic cell lines greatly increases ICAM-1 expression. Thus, ICAM-1 is preferentially expressed at sites of inflammation, and is not generally expressed by quiescent cells. ICAM-1 expression on dermal fibroblasts is increased threefold to fivefold by either interleukin 1 or gamma interferon at levels of 10 U/ml over a period of 4 or 10 hours, respectively. The induction is dependent on protein and mRNA synthesis and is reversible.

ICAM-1 displays molecular weight heterogeneity in different cell types with a molecular weight of 97 kd on fibroblasts, 114 kd on the mylemonocytic cell line U937, and 90 kd on the B lymphoblastoid cell JY. ICAM-1 biosynthesis has been found to involve an approximately 73 kd intracellular precursor. The non-N-glycosylated form resulting from tunicamycin treatment (which inhibits glycosylation) has a molecular weight of 55 kd. ICAM-1 isolated from phorbol ester stimulated U937 cells or from fibroblast cells yields an identical major product having a molecular weight of 60 kd after chemical deglycosylation. ICAM-1 monoclonal antibodies interfere with the adhesion of phytohemagglutinin blasts to LFA-1 deficient cell lines. Pretreatment of fibroblasts, but not lymphocytes, with monoclonal antibodies capable of binding ICAM-1 inhibits lymphocyte-fibroblast adhesion. Pretreatment of lymphocytes, but not fibroblasts, with antibodies against LFA-1 has also been found to inhibit lymphocyte-fibroblast adhesion.

ICAM-1 is, thus, the binding ligand of molecules of teh CD18 family of glycoproteins. It is inducible on fibroblasts and endothelial cells in vitro by inflammatory mediators such as IL-1, gamma interferon and tumor necrosis factor in a time frame consistent with the infiltration of lymphocytes into inflammatory lesions in vivo (Dustin, M. D., et. al., *J. Immunol* 137:245-254, (1986); Prober, J. S., et al., *J. Immunol* 137:1893-1896, (1986)). Further ICAM-1 is expressed on non-hematopoietic cells such as vascular endothelial cells, thymic epithelial cells, other epithelial cells, and fibroblasts and on hematopoietic cells such as tissue macrophages, mitogen-stimulated T lymphocyte blasts, and germinal center B-cells and dendritic cells in tonsils, lymph nodes and Peyer's patches (Dustin, M. L., et al., *J. Immunol* 137:245-254, (1986)). ICAM-1 is expressed on keratinocytes in benign inflammatory lesions such as allergic eczema, lichen planus, exanthema, urticaria and bullous diseases. Allergic skin reactions provoked by the application of a hapten on the skin to which the patient is allergic also revealed a heavy ICAM-1 expression on the keratinocytes. On the other hand toxic patches on the skin did not reveal ICAM-1 expression on the keratinocytes. ICAM-1 is present on keratinocytes from biopsies of skin lesions from various dermatological disorders and ICAM-1 expression is induced on lesions from allergic patch tests while keratinocytes from toxic patch test lesions failed to express ICAM-1.

Yet another aspect of the invention is the discovery that agents which prevent or inhibit cellular adhesion may be employed in the treatment of asthma.

One example of agents which may be used in accordance with the present invention are ICAM-1 and functional derivatives of ICAM-1. Since ICAM-1 mediates cellular adhesion by binding to a receptor molecule on the eosinophil cell surface, functional derivatives of ICAM-1 which can bind to the ICAM-1 receptor present on eosinophils will compete with the ICAM-1 on lung endothelial cells, thus attenuating cellular adhesion of the eosinophils, and providing a treatment for asthma.

A "functional derivative" of ICAM-1 is a compound which posses a biological activity (either functional or structural) that is substantially similar to a biological activity of ICAM-1. The term "functional derivatives" is intended to include the "fragments," "variants," "analogs," or "chemical derivatives" of a molecule. A "fragment" of a molecule such as ICAM-1, is meant to refer to any polypeptide subset of the molecule. Fragments of ICAM-1 which have ICAM-1 activity and which are soluble (i.e. not membrane bound) are especially preferred.

ICAM-1 is composed of 7 domains (Staunton, D. E. et al., *Immunol. Today* 9:213-215 (1988); Staunton, D. E. et al., *Cell* 52:925-934 (1988); Staunton, D. E. et al., *Cell* 56:849-854 (1989); Staunton, D. E. et al., *Tissue Antigens* 33:287 (1989), all of which references ar incorporated herein by reference). The domains of ICAM-1 are shown in FIG. 2. Domains 1 and 2 have been found to be important for the binding of ICAM-1 to its receptor molecule (Staunton, D. E. et al., *Tissue Antigens* 33:286 (1989); Staunton, D. E. et al., FASEB J. 3:a446 (1989) both of which references are incorporated herein by reference). In accordance with the present invention, ICAM-1 functional derivatives, and especially such derivatives which comprise fragments or mutant variants of ICAM-1 which possess both domains 1 and 2 can be used in the treatment or therapy of asthma. More preferred for such treatment or therapy are ICAM-1 fragments or mutant variants which contain domain 2 of ICAM-1. Most preferred for such treatment of therapy are ICAM-1 fragments or mutant variants which contain domain 1 of ICAM-1.

A "variant" of a molecule such as ICAM-1 is meant to refer to a molecule substantially similar in structure and function to either the entire molecule, or to a fragment thereof.

A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical. An "analog" of a molecule such as ICAM-1 is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). "Toxin-derivatized" molecules constitute a special class of "chemical derivatives." A "toxin-derivatized" molecule is a molecule (such as ICAM-1 or an antibody) which contains a toxin moiety. The binding of such a molecule to a cell brings the toxin moiety into close proximity with the cell and thereby promotes cell death. Any suitable toxin moiety may be employed; however, it is preferable to employ toxins such as, for example, the ricin toxin, the diphtheria toxin, radioisotopic toxins, membrane-channel-forming toxins, etc. Procedures for coupling such moieties to a molecule are well known in the art.

An additional example of agents which may be used in accordance with the present invention to treat asthma are LFA-1, Mac-1 or p150,95, or the functional derivatives of these molecules. Such molecules and their functional derivatives can provide a treatment for asthma by virtue of their capacity to bind to the ICAM-1 of endothelial cells, and thus impair the ability of such cells to mediate binding and adhesion of eosinophils.

Of special interest to the present invention are functional derivatives of LFA-1, Mac-1 or p150,95 which are soluble molecules. Of special interest are functional derivatives of these molecules which are heterodimers (containing both the alpha and beta subunits of the molecules) and monomeric derivatives capable of binding ICAM-1. Soluble heterodimers are especially preferred.

ICAM-1 and the members of the CD18 family of molecules are immunogenic molecules. Thus, it is possible to obtain antibodies capable of binding to ICAM-1 or members of the CD18 family of molecules. Such antibodies may be used in accordance with the methods of the present invention in the treatment of asthma.

Such antibodies may be obtained by introducing either the purified molecules (or cells which naturally express these molecules) into an appropriate animal, as by intraperitonaeal injection, etc. If desired, the serum of such an animal may be removed and used as a source of polyclonal antibodies capable of binding these molecules. It is, however, preferable to remove splenocytes from such animals, to fuse such spleen cells with a myeloma cell line and to permit such fusion cells to form a hybridoma cell which secretes monoclonal antibodies capable of binding ICAM-1 or members of the CD18 family of molecules.

The hybridoma cells, obtained in the manner described above may be screened as described above to identify desired hybridoma cells that secrete antibody capable of binding either to ICAM-1 or to members of the CD18 family of molecules (either the alpha of beta subunit).

Since such antibodies have the capacity to bind the ICAM-1 or its receptor, they (and their fragments having antigen binding ability, such as Fab, F(ag)$_2$, etc.) may be used to attenuate cellular adhesion, and thus provide an additional example of an agent which may be used in accordance with the present invention to treat asthma.

As indicated above, both polyclonal and monoclonal antibodies may be employed in accordance with the present invention. Of special interest to the present invention are antibodies to ICAM-1 (or their functional derivatives), or to members of the CD18 family (or their functional derivatives), which are produced in humans, or are "humanized" (i.e. non-immunogenic in a human) by recombinant or other technology. Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO86/011533; Cabilly, S. et al., European Patent Application 125,023; Better, M. et al., *Science* 240:1041-1043 (1988); Liu, A. Y. et al., *Proc. Natl. Acad. Sci. U.S.A.* 84:3439-3443 (1987); Liu, A. Y. et al., *J. Immunol.* 139:3521-3526 (1987); Sun, L. K. et al., *Proc. Natl. Acad. Sci. U.S.A.* 84:214-218 (1987); Nishimura, Y. et al., *Canc. Res.* 47:999-1005 (1987); Wood, C. R. et al., *Nature* 314:446-449 (1985)); Shaw et al., *J. Natl. Cancer Inst.* 80:1553-1559 (1988).

General reviews of "humanized" chimeric antibodies are provided by Morrison, S. L. (*Science,* 229:1202-1207

(1985)) and by Oi, V. T. et al., *BioTechniques* 4:214 (1986)).

Suitable "humanized" antibodies can be alternatively produced by CDR or CEA substitution (Jones, P. T. et al., *Nature* 321:552–525 (1986); Verhoeyan et al., *Science* 239:1534 (1988); Beidler, C. G. et al., *J. Immunol.* 141:4053–4060 (1988)).

The anti-asthma agents of the present invention may be obtained by natural processes (such as, for example, by inducing an animal, plant, fungi, bacteria, etc., to produce a non-immunoglobulin antagonist of ICAM-1, or by inducing an animal to produce polyclonal antibodies capable of binding to ICAM-1); by synthetic methods (such as, for example, by using the Merrifield method for synthesizing polypeptides to synthesize ICAM-1, functional derivatives of ICAM-1, or protein antagonists of ICAM-1 (either immunoglobulin or non-immunoglobulin)); by hybridoma technology (such as, for example, to produce monoclonal antibodies capable of binding to ICAM-1); or by recombinant technology (such as, for example, to produce the anti-asthma agents of the present invention in diverse hosts (i.e., yeast, bacteria, fungi, cultured mammalian cells, etc.), or from recombinant plasmids or viral vectors), or by proteolysis. The choice of which method to employ will depend upon factors such as convenience, desired yield, etc. It is not necessary to employ only one of the above-described methods, processes, or technologies to produce a particular anti-asthma agent; the above-described processes, methods, and technologies may be combined in order to obtain a particular anti-asthma agent.

Functional derivatives of ICAM-1, or a member of the CD18 family, having up to about 100 residues may be conveniently prepared by in vitro synthesis. If desired, such fragments may be modified by reacting targeted amino acid residues of the purifies or crude protein with an organic derivatizing agent that is capable of reacting with selected side chains or terminal residues. The resulting covalent derivatives may be used to identify residues important for biological activity. In the embodiments listed below, this aspect of the invention is described with reference to the functional derivatives of ICAM-1. Such methods may also be employed to produce functional derivatives of any member of the CD18 family of molecules.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diozole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivitization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method being suitable.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparginyl and glutaminyl residues by reaction with ammonium ions.

Derivatization with bifunctional agents is useful for crosslinking an ICAM-1 functional derivative molecule to a water-insoluble support matrix or surface for use int he method for cleaving an ICAM-1 functional derivatives fusion polypeptide to release and recover the cleaved polypeptide. Commonly used crosslinking agents include e.g., 1,1-bis(diazoacetyl)-2-phenylethane, glutaraldehyde, N-hydroxysuccinimide esters, for example, esters with 4-azidosalicyclic acid, homobifunctional imidoesters, including disuccinimidyl esters such as 3,3'-dithiobis(succinimidylpropionate), and bifunctional maleimides such as bis-N-maleimideo-1,8-octane. Derivatizing agents such as methyl-3-[(p-azidophenyl)-dithio]propionimidate yield photoactivatable intermediates that are capable of forming crosslinks in the presence of light. Alternatively, reactive water-insoluble matrices such ascyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or theonyl residues, methylation of the α-amino groups of lysine, arginine, and histidine side chains (T. E. Creighton, *Proteins: Structure and Molecule Properties,* W. H. Freeman & Co., San Francisco, pp. 79–86 (1983)), acetylation of the N-terminal amine, and, in some instances, amidation of the C-terminal carboxyl groups.

Functional derivatives of ICAM-1 having altered amino acid sequences can also be prepared by mutations in the DNA. The nucleotide sequences can also be prepared by mutations in the DNA. The nucleotide sequence which encodes the ICAM-1 gene is shown in FIG. 1. Such variants include, for example, deletions from, or insertions or substitutions of, residues within the amino acid sequence shown in FIG. 1. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP Patent Application Publication No. 75,444).

At the genetic level, these functional derivatives ordinarily are prepared by site-directed mutagenesis of nucleotides in the DNA encoding the ICAM-1 molecule, thereby producing DNA encoding the functional derivative, and thereafter expressing the DNA in recombinant cell culture. The functional derivatives typically exhibit the same qualitative biological activity as the naturally occurring analog. They may, however, differ substantially in such characteristics with respect to the normally produced ICAM-1 molecule.

While the site for introducing an amino acid sequence variation in predetermined, the mutation per se need not be predetermined. For example, to optimize the performance of a mutation at a given site, random mutagenesis may be conducted at the target codon or region and the expressed ICAM-1 functional derivatives screened for the optimal combination of desired activity. Techniques for making substitution mutations at predetermined sites in DNA having a known sequence are well known, for example, site-specific mutagenesis.

Preparation of an ICAM-1 functional derivative molecule in accordance herewith is preferably achieved by site-specific mutagenesis of DNA that encodes an earlier prepared functional derivatives or a nonvariant version of the protein. Site-specific mutagenesis allows the production of ICAM-1 functional derivatives through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (U.S.A.) 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as JM101 cells, and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertion (i.e., insertions within the complete ICAM-1 molecule sequence) may range generally from about 1 to 10 residues, more preferably 1 to 5. An example of a terminal insertion includes a fusion of a signal sequence, whether heterologous or homologous to the host cell, to the N-terminus of the molecule to facilitate the secretion of the ICAM-1 functional derivative from recombinant hosts.

The third group of functional derivatives are those in which at least one amino acid residue in the ICAM-1 molecule, and preferably, only one, has been removed and a different residue inserted in its place. Such substitutions preferably are made in accordance with the following Table 1 when it is desired to modulate finely the characteristics of the ICAM-1 molecule.

TABLE 1

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |

TABLE 1-continued

| Original Residue | Exemplary Substitutions |
| --- | --- |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the ICAM-1 molecule. However, when it is difficult to predict the exact effect of the substitution, deletion, or insertion in advance of doing so, one skilled in the art will appreciate that the effect will be evaluated by routine screening assays. For example, a functional derivative typically is made by site-specific mutagenesis of the native ICAM-1 molecule-encoding nucleic acid, expression of the variant nucleic acid in recombinant cell culture, and, optionally, purification from the cell culture, for example, by immunoaffinity adsorption on an anti-ICAM-1 molecule antibody column (to absorb the functional derivative by binding it to at least one remaining immune epitope).

The activity of the cell lysate or purified ICAM-1 molecule functional derivative is then screened in a suitable screening assay for the desired characteristic. For example, a change in the immunological character of the functional derivative, such as affinity for a given antibody, is measured by a competitive type immunoassay. Changes in immunomodulation activity are measured by the appropriate assay. Modifications of such protein properties as redox or thermal stability, biological half-life, hydrophobicity, susceptibility to proteolytic degradation or the tendency to aggregate with carriers or into multimers are assayed by methods well known to the ordinarily skilled artisan.

C. Administration of the Compositions of the Present Invention

The therapeutic effects of the anti-asthma agents of the present invention may be obtained by providing such agents to a patient by any suitable means (i.e. intravenously, intramuscularly, subcutaneously, enterally, or parenterally). It is preferred to administer the agents of the present invention intranasally as by nasal spray, swab, etc. It is especially preferred to administer such agents by oral inhalation, or via an oral spray or oral aerosol. When administering agents by injection, the administration may be by continuous infusion, or by single or multiple boluses.

The therapeutic advantages of any of the above-described agents can be augmented through the use of functional derivatives possessing additional amino acid residues added to enhance coupling to carrier or the enhance the activity of the agent. The scope of the present invention is further intended to include functional derivatives of ICAM-1 which lack certain amino acid residues, or which contain altered amino acid residues, so long as such derivatives exhibit the capacity to affect cellular adhesion.

The antibodies of the present invention and the ICAM-1 molecule and the members of the CD18 family disclosed herein are said to be "substantially free of natural contaminants" if preparations which contain them are substantially free of materials with which these products are normally and naturally found.

The present invention extends to the use of antibodies, and biologically active fragments thereof, (whether polyclonal or monoclonal) which are capable of binding to ICAM-1 or to a member of the CD18 family in the treatment of asthma.

In providing a patient with antibodies, or fragments thereof, capable of binding to ICAM-1 or to a member of the CD18 family, or when providing ICAM-1 or a member of the CD18 family (or a fragment, variant, or derivative thereof) to a recipient patient, the dosage of administered agent will vary depending upon such factors as the patient's age, weight, height, sex, general medical condition, previous medical history, etc. In general, it is desirable to provide the recipient with a dosage of agent which is in the range of form about 1 pg/kg to 10 mg/kg (body weight of patient), although a lower or higher dosage may be administered. The therapeutically effective dose can be lowered by using combinations of the above-described agents (such as, for example, if anti-ICAM-1 antibody is additionally administered with an anti-LFA-1 antibody). As used herein, one compound is said to be additionally administered with a second compound when the administration of the two compounds is in such proximity of time that both compounds can be detected at the same time in the patient's serum.

The anti-asthma agents of the present invention are intended to be provided to recipient subjects in an amount sufficient to lessen or attenuate the severity, extent or duration of the asthma symptoms.

The antibody agents of the invention, or their fragments, may be administered either alone or in combination with one or more additional anti-asthma agents (such as methylxanthines (such as thiophylline), beta-adrenergic agonists (such as catecholamines, resorcinols, saligenins, and ephedrine), glucocorticoids (such as hydrocortisone), chromones (such as cromolyn sodium) and anticholinergics (such as atropine, in order to decrease the amount of such agents needed to treat the asthma symptoms.

The administration of the agent(s) of the invention may be for either a "prophylactic" or "therapeutic" purpose. When provided prophylactically, the agent(s) are provided in advance of any asthma symptom. The prophylactic administration of the agent(s) serves to prevent or attenuate any subsequent asthmatic response. When provided therapeutically, the agent(s) are provided at (or shortly after) the onset of a symptom of asthma. The therapeutic administration of the compound(s) serves to attenuate any actual asthmatic episode. The agents of the present invention may, thus, be provided either prior to the onset of an anticipated asthmatic episode (so as th attenuate the anticipated severity, duration or extent of the episode) or after the initiation of the episode.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The agents of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition suitable for effective administration, such composition will contain an effective amount of anti-ICAM antibody or ICAM-1 molecule, or their functional derivatives, together with a suitable amount of carrier vehicle.

Additional pharmaceutical methods may be employed to control the duration of action. Control release preparations may be achieved through the use of polymers to complex or absorb anti-ICAM-1 antibody or ICAM-1, or their functional derivatives. The controlled delivery may be exercised by selecting appropriate macromolecules (for example polyesters, polyamino acids, polyvinyl, pyrrolidone, ethylenevinyl-acetate, methylcellulose, carboxymethylcellulose, or protamine, sulfate) and the concentration of macromolecules as well as the methods of incorporation in order to control release. Another possible method to control the duration of action by controlled release preparations is to incorporate anti-ICAM-1 antibody or ICAM-1 molecules, or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Having now generally described the invention, the same will be more readily understood through reference to the following examples which are provided by way of illustration, and are not intended to be limiting of the present invention, unless specified.

EXAMPLE 1

Lung Eosinophil Adhesion Reactions Depend on CD11 and ICAM-1 Cell Adhesion Molecules In order to evaluate the requirement for cell adhesion of eosinophils in their migratory and cytotoxic function, eosinophil adhesion in vitro was tested. In particular, the role of the CD18 family of cellular adhesion molecules, and of ICAM-1, in primate eosinophil adhesion to protein coated plastic and to human endothelium was examined.

Eosinophils were obtained by bronchoalveolar lavage from adult male cynomegalus monkeys (Macaca fascicularis), purified (>93% by morphology) on a Percoll continuous density gradient, washed, and added to 96 well flat-bottom tissue culture plates at a concentration of $5 \times 10^3$ cells/well. After a 60 min. incubation at 37° C., the non-adherent cells were removed using a plate washer. Adherent cells were enumerated visually (no aggregation or degranulation was observed) and by a colorimetric assay which measures eosinophil peroxidase (EPO).

Figure 3:
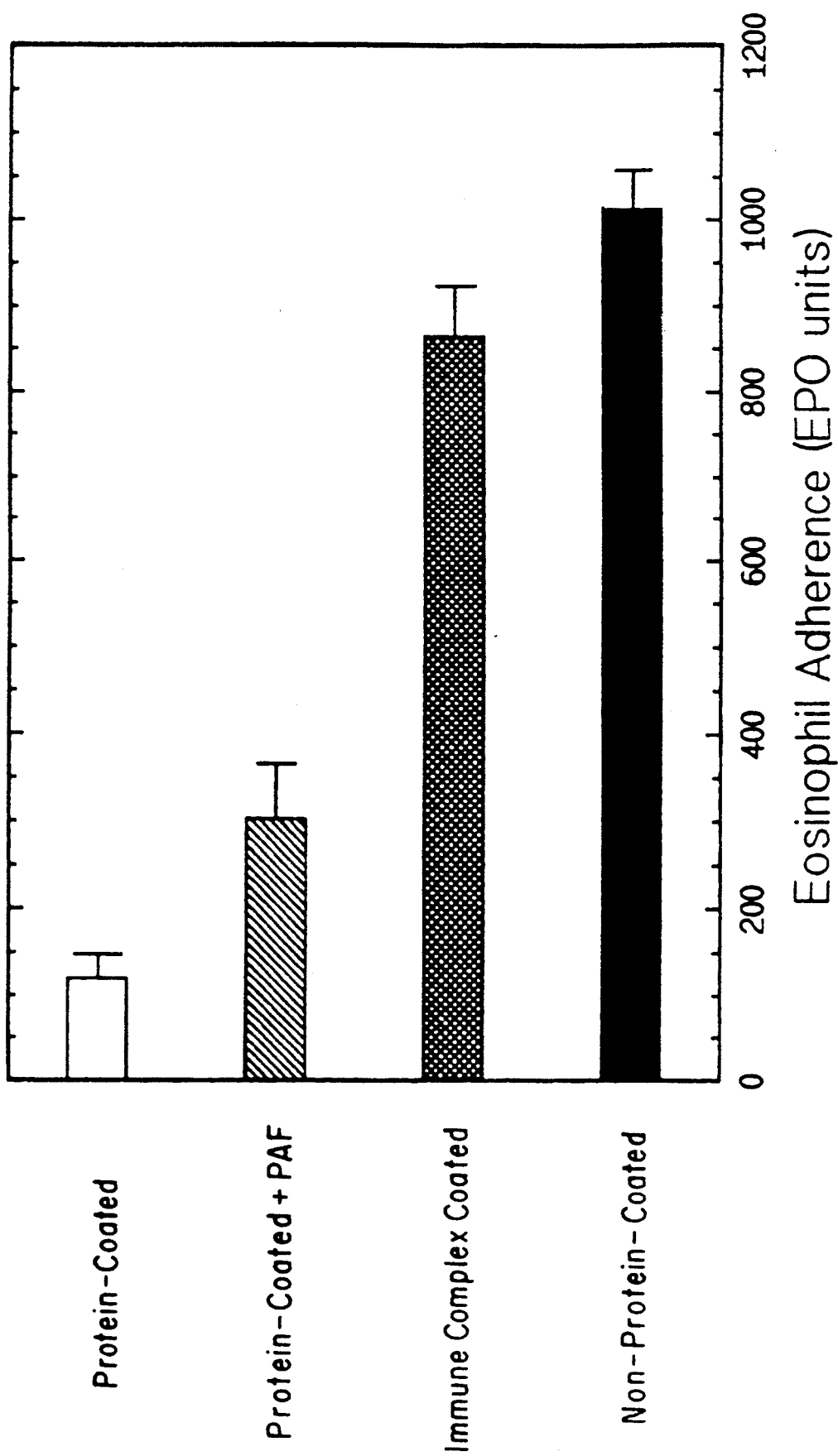
FIG. 3 shows eosinophil adherence to flat bottom tissue culture plate wells protein-coated with no stimulus, protein-coated with PAF ($10^{-7}$M) stimulus, immune complex (IC) coated and stimulus, and non-coated with no stimulus. Adhered cells were quantitated by a colorimetric assay for eosinophil peroxidase (EPO) as means EPO units $\pm$S.D.

The eosinophils spontaneously adhered and spread on the bottom of untreated wells or of wells coated with immune complexes (made from Ascaris extract and serum from an Ascaris-immune monkey). In contrast, eosinophils did not adhere well to wells coated with proteins, including bovine serum albumin, normal monkey serum, or Ascaris extract. Of various soluble stimuli tested, Platelet Activating Factor (PAF) induced the most pronounced and consistent adherence of eosinophils to protein-coated wells (FIG. 3).

The role of CD18 adhesion molecules and of ICAM-1 in this adherence process was tested using monoclonal antibodies reactive with each of these membrane glycoproteins. Antibodies used included: R3.3 and R15.7 (anti-CD18); R3.1 (anti-CD11a); M1/70 and LM2/1 (anti-CD11b); RR1/1 and R6.5.D6 (ATCC HB 9580) (anti-ICAM-1); and W6/32 (anti HL-A class I).

Figure 4:
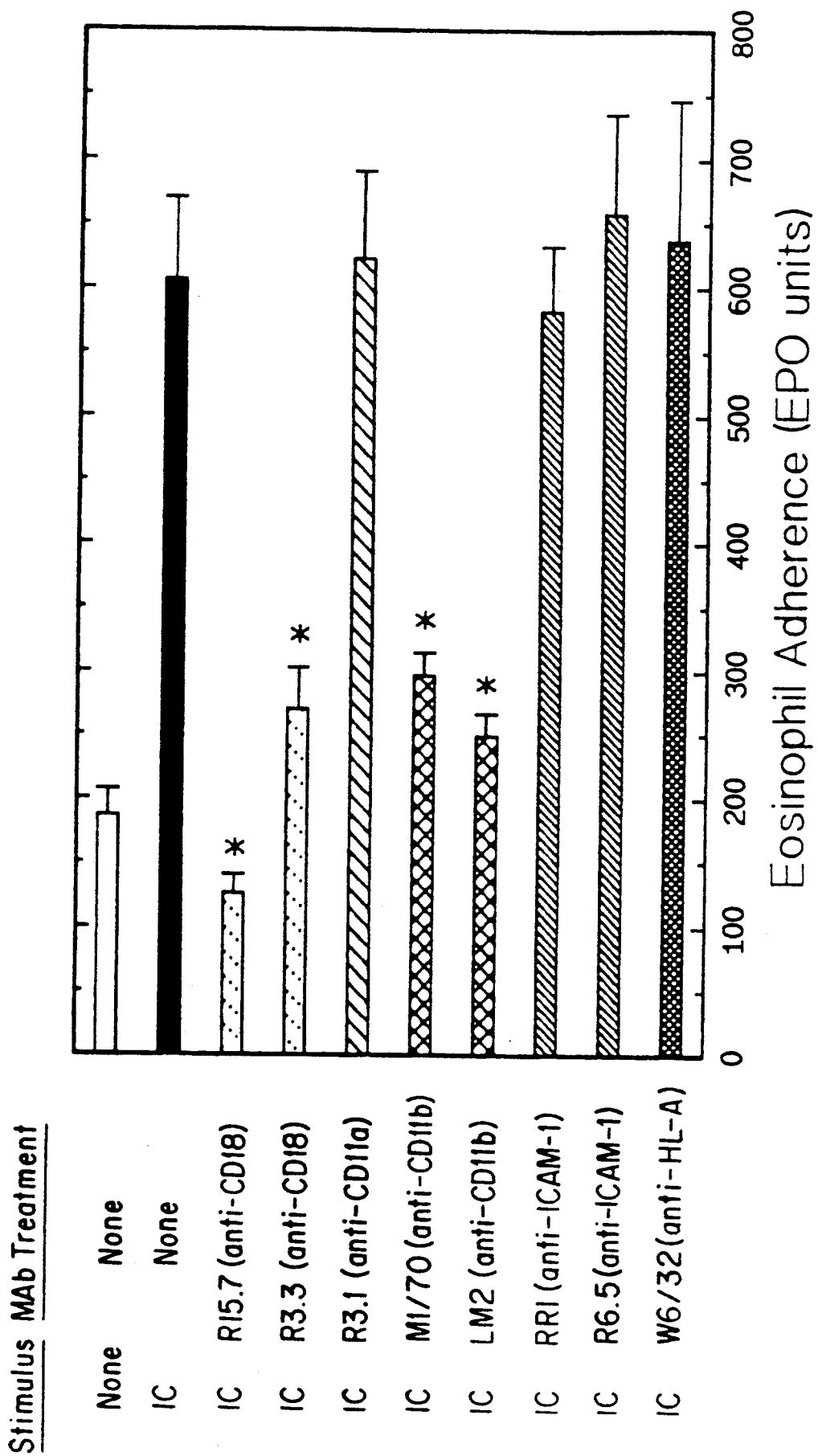
FIG. 4 shows the effect of various monoclonal antibodies (MAbs) (supernatant 1:4 dilution) on eosinophil adherence to flat bottom tissue culture plate wells coated with immune complexes (IC). Adhered cells were quantitated by a colorimetric assay for eosinophil peroxidase (mean EPO units $\pm$S.D.). Statistically significant attenuation of adherence is signified by an asterisk.

Adhesion of the eosinophils to immune complex-coated wells appeared to be CD11b-dependent, since mAbs against CD11b and CD18 inhibited adhesion while mAbs against CD11a, ICAM-1, and HL-A did not (FIG. 4). Identical results were obtained using eosinophils activated by soluble stimuli, including PAF, and protein-coated wells.

Figure 5:
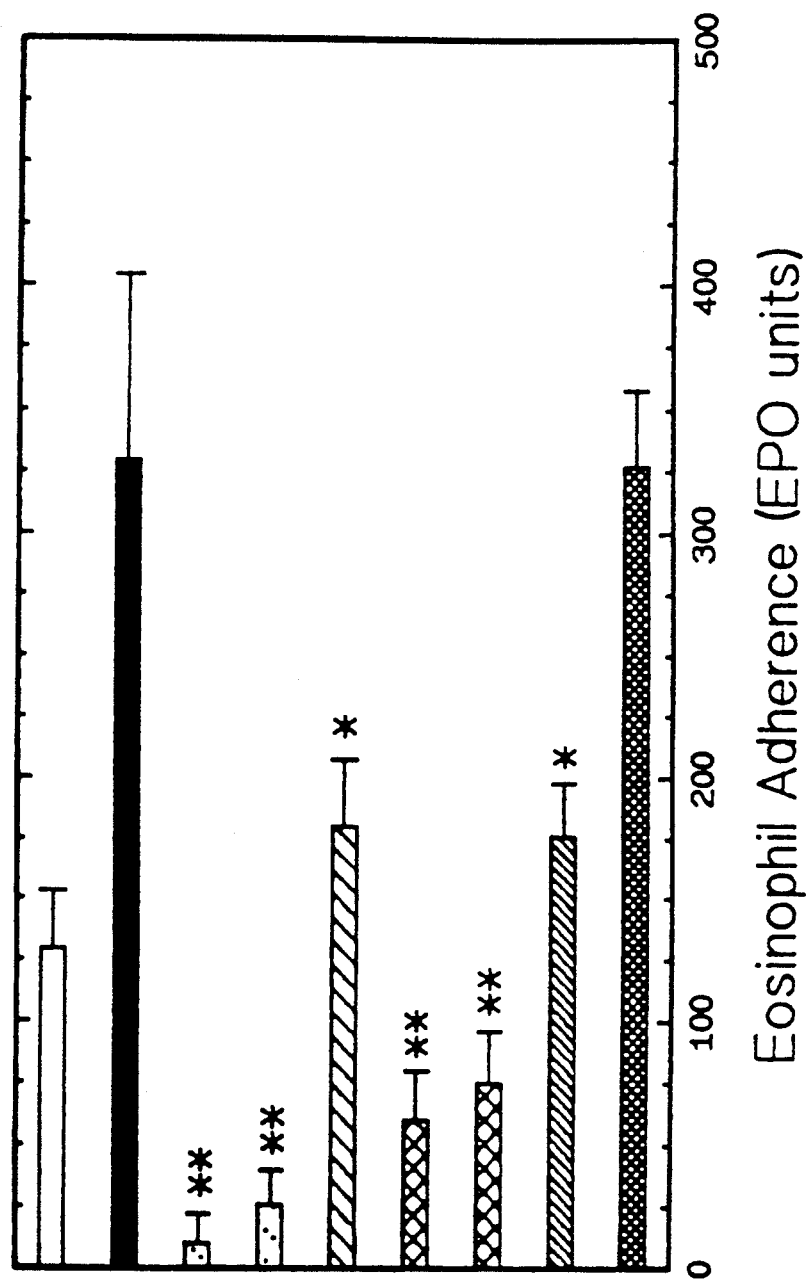
FIG. 5 shows the effect of various monoclonal antibodies (MAbs) (supernatant 1:4 dilution) on PAF ($10^{-7}$M) induced eosinophil adherence to LPS (10 ng/ml)-stimulated and glutaraldehyde-fixed endothelium. Adhered cells were quanititated by a colorimetric assay for eosinophil peroxidase (EPO units $\pm$S.D.). Statistically significant attenuation of adherence is signified by an asterisk.

Adhesion of eosinophils to endothelial cells activated by LPS (10 ng/ml) and fixed with glutaraldehyde was also tested. Human umbilical vein endothelial cells were prepared as described by Smith, C. W. et al., (J. Clin. Invest. 82:1746 (1988) which reference is incorporated herein by reference). Adhesion of eosinophils induced by PAF ($10^{-7}$M) to such activated endothelial cells was partially inhibited by mAbs against CD11a, CD11b, and ICAM, completely inhibited by anti-CD18, and not inhibited by anti-HL-A (FIG. 5). These experiments revealed that the observed adhesion was partially dependent on CD11a, CD11b, and ICAM-1.

In summary, primate lung eosinophils behave nearly identically to human neutrophils in membrane adhesion reactions involving CD11a, CD11b, and ICAM-1. The CD18 family of CAMs therefore plays a major role in eosinophil adherence and is responsible to selective tissue accumulation of eosinophils in LAD patients.

EXAMPLE 2

Role of ICAM-1 in Eosinophil Infiltration

In order to demonstrate that ICAM-1 contributed to the eosinophil infiltration, airway epithelium desquamation and increased airway responsiveness that characterize the airway inflammation underlying bronchial asthma, the effect of monoclonal antibodies reactive with ICAM-1 on asthma in primates was investigated. Specifically, (a) the contribution of ICAM-1 to eosinophil adhesion to vascular endothelium in vitro, (b) the induction of ICAM-1 on airway epithelium in vitro and in vivo as well as on bronchial vascular endothelium in vivo, and (c) the contribution of ICAM-1 to the eosinophil infiltration and increase in airway responsiveness induced by multiple inhalations of antigen in vivo were investigated.

Primate lung eosinophils were stimulated with platelet-activating factor (PAF, $10^{-7}$M), and incubated in the presence of lipopolysaccharide (LPS, 10 ng/ml) stimulated cultured human umbilical vein endothelial cells (HUVECs) in order to assay for celular adhesion. Eosinophils were obtained by bronchoalveolar lavage from adult male cynomolgus monkeys (*Macaca fascicularis*) with airway eosinophilia, purified (morphologically >95% pure) on a Percoll continuous density gradient (Riding, G. A. et al., *J. Immunol. Meth.* 46:113 (1981)), washed and added to 96 well flat bottom tissue culture plates ($5 \times 10^3$ cells/well). After a 60 minute incubation at 37° C., the non-adherent cells were removed by an automated plate washer. Adherent cells were quantitated visually and by a colorimetric assay for eosinophil peroxidase, EPO (Strath, M. et al., *J. Immunol. Meth.* 83:209 (1985)). Human umbilical vein endothelial cells were isolated, cultured to a confluent monolayer in each well, stimulated for 4 hours with LPS and finally fixed in 1% glutaraldehyde (Smith, C. W. et al., *J. Clin. Invest.* 82:1746 (1988)). Immune complex wells were made by coating with Ascaris extract followed by serum from an Ascaris-sensitive monkey.

Figure 6A:
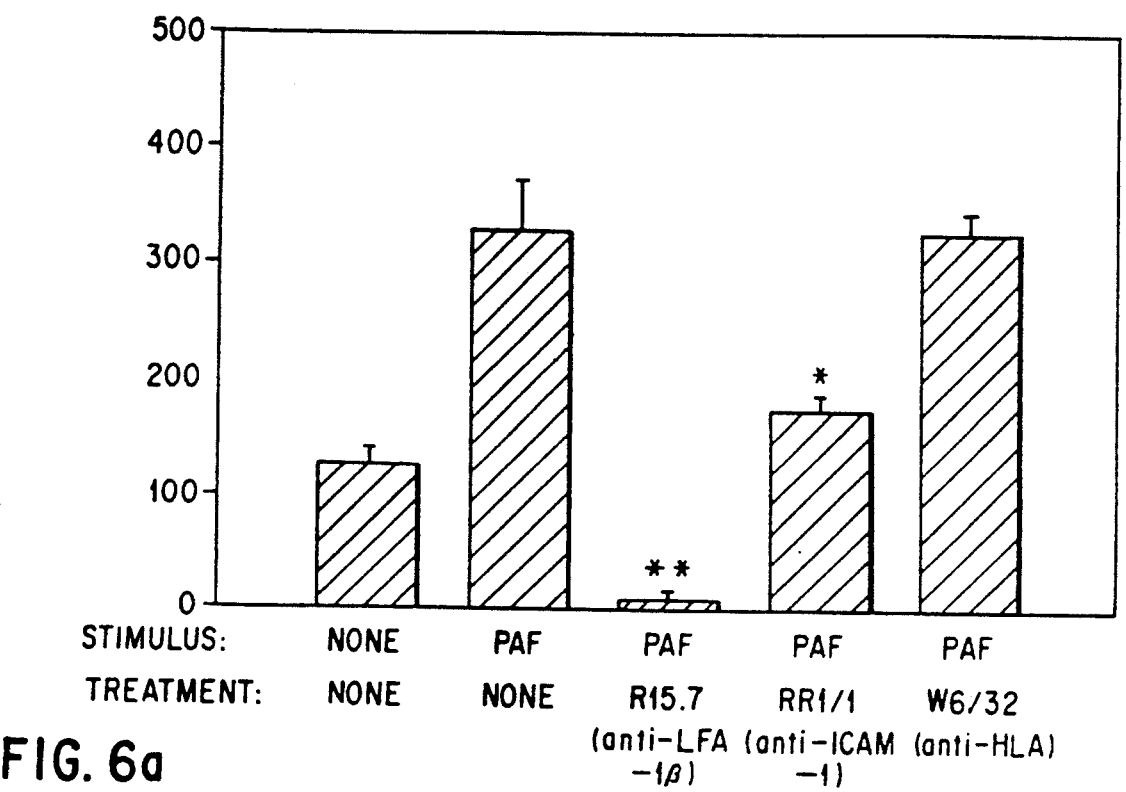
FIG. 6, panels a and b show the effect of anti-ICAM-1 (RR1/1), anti-LFA-1 beta (R15.7) and anti-HLA class 1 (W6/32) monoclonal antibodies (supernatant 1:4 dilution) an (6A) platelet-activating factor (PAF, $10^{-7}$M) induced eosinophil adhesion to lipopolysaccharide (LPS, 10 ng/ml)-stimulated human umbilical vein endothelium, and (6B) eisoniphil adhesion to flat bottom tissue culture plate wells coated with Ascaris extract (no stimulus) or immune complex (IC stimulus). Statistically significant attenuation of adherence is signified by an asterisk.

Adhesion was found to be significantly inhibited by the anti-ICAM-1 monoclonal antibody RR1/1 (Rothlein, R. et al., *J. Immunol.* 137:1270 (1986); Marlin, S. D. et al., *Cell* 51:813 (1987)) (FIG. 6A). In contrast, the anti-HLA class I control monoclonal antibody W6/32, which also binds to HUVECs (Smith, C. W. et al., *J. Clin Invest.* 82:1746 (1988)), did not inhibit eosinophil adherence (FIG. 6A).

Figure 6B:
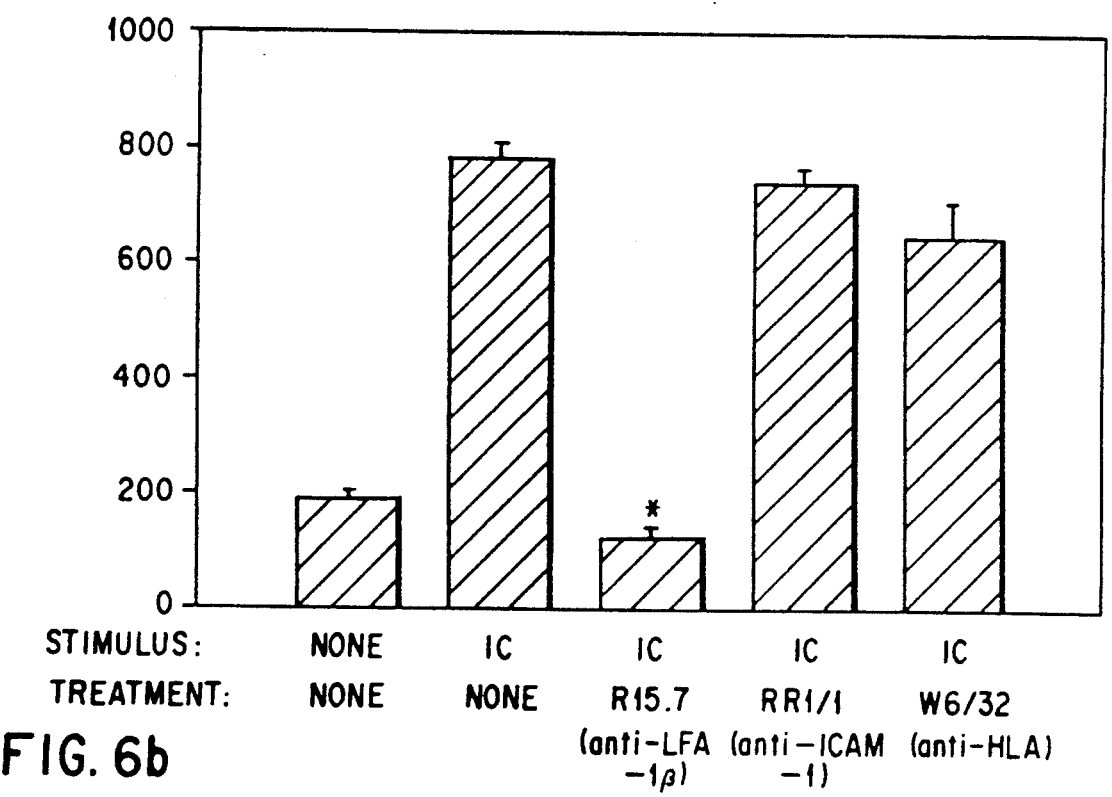

Adherence of primate lung eosinophils to immune complex coated plastic was not inhibited by RR1/1 (FIG. 6B) demonstrating the specificity of the inhibition of adherence to endothelium. These results indicate that ICAM-1 is important for eosinophil adhesion to endothelium and thus may contribute to eosinophil migration into inflamed tissues in vivo.

In addition to being required for migration into tissues, leukocyte adhesion is a prerequisite for cytotoxic tissue injury. Inhibition of adhesion of effector to target cells has been reported to reduce both lymphocyte and granulocyte mediated killing in vitro and allograft rejection in vivo (Martz, E. et al., *J. Immunol.* 133:2972 (1984)). Since eosinophils and their products have been implicated in airway epithelium desquamation (Frigas, E. et al., *J. Allergy Clin. Immunol.* 77:527 (1986)) which in turn is strongly linked with airway hyperresponsiveness (Laitinen, L. A. et al., *Am. Rev. Respir. Dis.* 137:62 (1988)) and asthma symptoms (Hargreave, F. E. et al., *J. Allergy Clin. Immunol.* 68:347 (1981); Boulet, L-P et al., *J. Allergy Clin. Immunol.* 71:399 (1983); Chan-Yeung, M. et al., *Am. J. Med.* 72:411 (1982); Frigas, E. et al., *J. Allergy Clin. Immunol.* 77:527 (1986)), the effects of various pro-inflammatory cytokines on ICAM-1 induction on airway epithelial cells in vitro was investigated.

Using an ELISA assay (Rothlein, R. et al., *J. Immunol.* 141:1665 (1988)) and the anti-ICAM-1 monoclonal antibodies RR1/1 and R6.5 (Smith, C. W. et al., *J. Clin. Invest.* 82:1746 (1988)) it was found that 16 hour stimulation with interleukin-1 bet (IL-1b), human recombinant tumor necrosis factor alpha (TNFa), and human recombinant interferon gamma (IFNg) enhanced ICAM-1 expression on a monolayer of cultured monkey bronchus epithelial cells (Table 2).

Table 2 shows the effects of pro-inflammatory cytokines on induction of ICAM-1 on bronchial epithelial cells in vitro. The rhesus monkey bronchus epithelial cell line 4MBr-5 (obtained from American Type Culture Collection) was cultured to a confluent monoleyer and then stimulated for 16 hours with IL-1b, TNFa or IFNg. ELISA assays for ICAM-1 [monoclonal antibodies RR1/1 (Rothlein, R. et al., *J. Immunol.* 137:1270 (1986); Marlin, S. D. et al., *Cell* 51:813 (1987)) and R6.5 (Smith, C. W. et al., *J. Clin. Invest.* 82:1746 (1988))] and LFA-1 alpha [monoclonal antibody R3.1 (Rothlein, R. et al., *J. Immunol.* 141:1665 (1988))] expression were performed as previously described (Rothlein, R. et al., *J. Immunol.* 141:1665 (1988)). The numbers represent the mean of optical density units (relative to normal mouse gamma globulin background) for duplicate cultures and is representative of four individual experiments.

TABLE 2

| Stimulus | Concentration | Optical Density Units | | |
|---|---|---|---|---|
| | | RR1/1 (anti-ICAM-1) | R6.5 (anti-ICAM-1) | R3.1 (anti-LFA-la) |
| none | — | 92 | 206 | −27 |
| IL-1b | 0.1 units/ml | 130 | 253 | −33 |
| | 1 unit/ml | 166 | 253 | −32 |
| | 10 units/ml | 149 | 322 | −37 |
| TNFa | 1 unit/ml | 100 | 236 | −30 |
| | 10 units/ml | 131 | 266 | −29 |
| | 100 units/ml | 159 | 346 | −31 |
| | 1000 units/ml | 178 | 416 | −36 |
| IFNg | 0.1 units/ml | 138 | 276 | −16 |
| | 1 unit/ml | 263 | 423 | −17 |
| | 10 units/ml | 413 | 673 | −26 |
| | 100 units/ml | 576 | 940 | −27 |

The time course of enhanced ICAM-1 expression (Table 3) was found to be similar to that previously reported for HUVECs in vitro (Smith, C. W. et al., *J. Clin. Invest.* 82:1746 (1988)) and human skin keratinocytes in vivo (Wantzin, G. L. et al., *J. Am. Acad. Dermatol.* 20:782 (1089)). As expected, the anti-LFA-1 alpha monoclonal antibody R3.1 (Rothlein, R. et al., *J. Immunol.* 141:1665 (1988)) did not bind to unstimulated or stimulated bronchial epithelium (Table 2). These results suggest that ICAM-1 could contribute to leukocyte (e.g., eosinophil) mediated desquamation of airway epithelium in vivo.

Table 3 shows the time course for the induction of ICAM-1 on bronchial epithelial cells in vitro. The rhesus monkey bronchus epithelial cell line 4MBr-5 (obtained from American Type Culture Collection) was cultured to a confluent monolayer and then stimulated for various time period with IL-1b (10 ng/ml) or IFNg (10 units/ml). An ELISA assay for ICAM-1 expression [monoclonal antibody R6.5 (Smith, C. W. et al., *J. Clin. Invest.* 82:1746 (1988))] was performed as previously described (Rothlein, R. et al., *J. Immunol.* 141:1665 (1988)). The numbers represent the mean of optical density units (relative to normal mouse gamma globulin background) for triplicate cultures and is representative of two individual experiments.

TABLE 3

| Stimulation Time | Stimulus | |
| (hours) | IL-1b | IFNg |
| --- | --- | --- |
| 0 | 215 | 215 |
| 2 | 240 | 250 |
| 4 | 296 | 349 |
| 8 | 364 | 349 |
| 16 | 417 | 826 |
| 24 | 369 | 812 |
| 48 | 472 | 672 |

EXAMPLE 3

Contribution of ICAM-1 to Desquamation In Vivo

To further investigate the ability of ICAM-1 to contribute to eosinophil-mediated desquamation of airway epithelium in vivo, immunohistochemical staining was conducted to determine if multiple inhalations of antigen induce ICAM-1 expression on airway epithelium in vivo.

Tissues were stained using a modification of a previously described protocol (Wantzin, G. L. et al., *J. Am. Acad. Dermatol.* 20:782 (1989)). Briefly, tissue specimens were removed and frozen in liquid nitrogen. After cryo-sectioning, 5-10 micron sections were fixed in acetone for 10 minutes and either stained immediately or stored at 20° C. Staining was performed using the Biotein-Strept Avidin System kit according to manufactures protocols (BioGenex, Calif.). Primarily antibody was incubated with tissue as undiluted culture supernatants (RPMI 1640 medium with 10% FBS) for one hour at room temperature. Blocking for non-specific protein binding was accomplished by applying normal goat serum. AEC (3-amino-9-ethylcarbazole) was used as a substrate and the sections were counterstained with Meyer's Hematoxylin.

Intense staining for ICAM-1 was found on both the epithelium (basilateral portion only) and on the vascular endothelium of a trachea section taken from an Ascaris antigen sensitive monkey twenty minutes after the third of three alternate day Ascaris inhalations. Staining for LFA-1 alpha (Anderson, D. C. et al., *J. Inf. Dis.* 152:668 (1985); Anderson, D. C. et al., *Ann. Rev. Med.* 38:175 (1987); Todd, R. F. et al., *Hematol./Oncol. Clinics N. Amer.* 2:13 (1988)) but not on airway epithelium (Table 2) revealed a leukocyte infiltration in the interstitium that appeared to be most marked just below the epithelial basement membrane. In addition leukocytes were notable between epithelial cells primarily at the basilateral portion of the epithelium where ICAM-1 staining was most pronounced. Little or nor nonspecific staining was observed using mouse serum. Staining (using ICAM-1, LFA-1 alpha and mouse serum) in a trachea section taken from an Ascaris-sensitive monkey twenty minutes after a single inhalation of Ascaris, revealed, as expected based on the time required for its expression (see Table 3 and references Wantzin, G. L. et al., *J. Am. Acad. Dermatol.* 20:782 (1989); Smith, C. W. et al., *J. Clin. Invest.* 82:1746 (1988), which references are incorporated herein by reference), little or no ICAM-1 staining was found on the epithelium or vascular endothelium in this section.

In addition, although pockets of leukocyte infiltration were found, leukocytes were not accumulated just below the epithelial baseline membrane and were not found between epithelial cells. Thus, these immunohistochemical staining results further suggest an ICAM-1 dependent eosinophil-epithelial cell interaction may contribute to the desquamation of airway epithelium found in asthmatics.

EXAMPLE 4

In Vivo Effect of ICAM-1 on Asthma

Having demonstrated a potential role for ICAM-1 in the pathogenesis of airway hyperresponsiveness and asthma using the in vitro and immunohistochemical protocols described above, the in vivo effect of anti-ICAM-1 antibodies was investigated. For these studies, an asthma animal model was employed. The model may be used with any mammal, but it is most preferable to employ primates in the model. To induce an asthmatic episode, inhalations of antigen were provided to a monkey on three alternate days. This regimen induced a consistent (usually greater than 8 fold) increase in airway responsiveness to inhaled methacholine in monkeys (Wegner, C. D. et al., *Am. Rev. Respir. Dis.* 139:A324 (1989), which reference is incorporated herein by reference). This increase in airway responsiveness is preceded by an intense eosinophil infiltration and is similar in magnitude to that induced in asthmatics during the pollen season (Boulet, L-P et al., *J. Allergy Clin. Immunol.* 71:399 (1983); Sotomayor, H. et al., *Am. Rev. Respir. Dis.* 130:56 (1984)) or on continued exposure to occupational allergens (Chan-Yeung, M. et al., *Am. J. Med.* 72:411 (1982); Lam, S. et al., *J. Allergy Clin. Immunol.* 72:134 (1983); Lam, S. et al., *J. Allergy Clin. Immunol.* 63:28 (1979)). In lieu of methacholine, histamine or other similar componds and methacholine equivalents can be employed.

Using this animal model, the effect of the anti-ICAM-1 monoclonal antibody R6.5 on eosinophil infiltration and the induction of airway hyperresponsiveness in vivo was investigated.

In accordance with the model, airway cell composition and airway responsiveness were determined three days prior to (Day 0) and three days after (Day 10) three alternate day (Day 3, 5 and 7) inhalations of antigen (Wegner, C. D. et al., *Am. Rev. Respir. Dis.* 139:A324 (1989)). Airway cell composition was measured by bronchoalveolar lavage (BAL). Airway responsiveness was measured by determining the concentration ($PC_{100}$) of inhaled methacholine that caused a 100% increase in respiratory system resistance. R6.5 was administered intravenously at 1.76 mg/kg daily on Days 2-9. Studies with R6.5 treatment were compared to bracketing control studies performed on each animal.

Figures 7A, 7B:
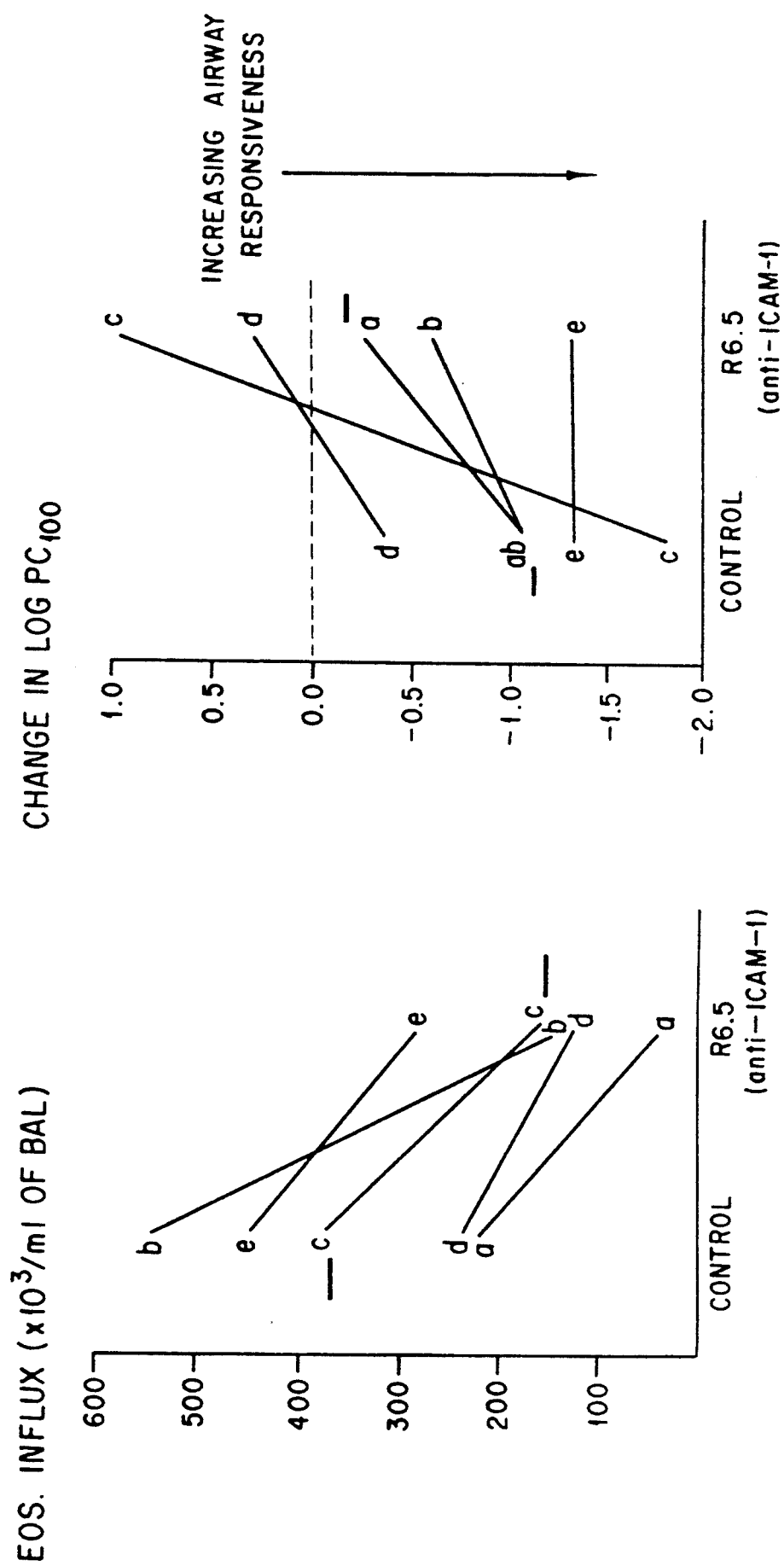
FIG 7, panels a and b show the effect of the anti-ICAM-1 monoclonal antibody R6.5 on the (7A) airway eosinophil infiltration and (7B) increase in airway responsiveness (decrease in methacholine $PC_{100}$) induced by three alternate day inhalations of Ascaris in Ascaris-sensitive cynomegalus monkeys (*Macaca fascicularis*). Studies with R6.5 treatment are compared to bracketing control studies performed on each animal.

R6.5 (anti-ICAM-1) treatment attenuated the eosinophil infiltration in all five animals studies (FIG. 7A). The increase in airway responsiveness (decrease in inhaled methacholine $PC_{100}$) was also inhibited in all five animals, markedly in four (FIG. 7B). Surprisingly, in two animals (c and d) airway responsiveness not only did not increase (as it had in control studies) but actually decreased (methacholine $PC_{100}$ increased) with R6.5 treatment, despite the multiple inhalations of antigen, demonstrating a reversal of an elevated basal airway responsiveness in these animals.

In summary, these results demonstrate that ICAM-1 is selectively induced on chronically inflamed tracheal vascular endothelium in vivo, that ICAM-1 contributes to eosinophil adhesion to vascular endothelium in vitro, and that an anti-ICAM-1 monoclonal antibody attenuates inhaled antigen-induced eosinophil infiltration in vivo. Furthermore, ICAM-1 expression is enhanced on cytokine stimulated airway epithelium in vitro and selectively induced on chronically inflamed tracheal epithelium in vivo indicating the ICAM-1 may contribute to airway epithelium desquamation in vivo. An anti-ICAM-1 monoclonal antibody was abvle to inhibit the increase in airway responsiveness induced by multiple inhalations of antigen in monkeys.

These results indicate that ICAM-1 plays a pivotal role in the pathogenesis of airway hyperresponsiveness and asthma. ICAM-1 similarly contributes to the onset and progression of other diseases characterized by airway inflammation [e.g., chronic bronchitis, emphysema, idiopathic pulmonary fibrosis, etc. (Guenter, C. A. et al., *Am. Rev. Respir. Dis.* 123:79 (1981); Rossi, G. A. et al., *Am. Rev. Respir. Dis.* 129:850 (1984); Hunninghake, G. W. et al., *Am. J. Pathol.* 97:149 (1979); Hunninghake, G. W. et al., *Am. Rev. Respir. Dis.* 123:407 (1981))] or eosinophil infiltration and tissue sensitization/destruction [e.g., rhinitis, nasal polyposis, chronic urticaria and atopic dermatitis (Mygind, N., *Allergy* 34:195 (1979); Mullarkey, M. F. et al., *J. Allergy Clin. Immunol.* 65:122 (1980); Peters, M. S. et al., *J. Invest. Dermatol.* 81:39 (1983); Leiferman, K. M. et al., *N. Engl. J. Med.* 313:282 (1985); Spry, C. J. F. et al., *Int. Archs. Allergy appl. Immun.* 77:252 (1985))]. Thus, agents which prevent or attenuate such cellular adhesion may be employed in the treatment of these diseases in the same manner as they may be used to treat asthma.

EXAMPLE 5

Effects of Single and Multiple Inhalations of Antigen on Airway Responsiveness in Monkeys In animals (Lanes, S. et al., *J. Appl. Physiol.* 61:864-872 (1986), Marsh, W. R. et al., *Amer. Rev. Respir. Dis.* 131:875-879 (1985)), as well as in man (Cartier, A. et al., *J. Allergy Clin. Immunol.* 70:170-177 (1982), Cockcroft, D. W. et al., *Clinical Allergy* 7:503-513 (1977), a single inhalation f an allergen can cause a mild (2-6 fold) increase in airway responsiveness. Repeated allergen exposures, such as those that occur in man during the pollen season (Boulet, L.-P. et al., *J. Allergy. Clin. Immunol.* 71:399-406 (1983), Sotomayor, H. et al., *Amer. Rev. Respir. Dis.* 130:56-58 (1984)) or in an occupational setting (Chan-Yeung, M. et al., *Amer. J. Med.* 72:411-415 (1982), Lam, S. et al., *J. Allergy Clin. Immunol.* 72:134-139 (1983), Lam, S. et al., *J. Allergy Clin. Immunol.* 63:28-34 (1979)), have been reported to cause greater (often ±10 fold) increases in airway responsiveness.

Multiple (4 weekly) instillations of antigen coated beads induce a 10 fold increase in airway responsiveness in monkeys (Gundel, R. H. et al., *Amer. Rev. Respir. Dis.* (1989), which reference is incorporated herein by reference).

In order to more develop a useful animal asthma model, the effects of single and multiple antigen inhalations on airway responsiveness to inhaled methacholine in monkeys was investigated. Since airway inflammation (Marsh, W. R. et al., *Amer. Rev. Respir. Dis.* 131:875-879 (1985), Sotomayor, H. et al., *Amer. Rev. Respir. Dis.* 130:56-58 (1984), Lazarus, S., *Amer. J. Med.* 81:2-7 (1986), O'Byrne, P. M., *Chest* 90:575-577 (1986)), especially eosinophil infiltration (Gundel, R. H. et al., *Amer. Rev. Respir. Dis.* (1989), DeMonchy, J. G. R. et al., *Amer. Rev. Respir. Dis.* 131:373-376 (1985), Wardlaw, A. J. et al. *Amer. Rev. Respir. Dis.* 137:62-69 (1988)), has been hypothesized to play a role in the pathogenesis of airway hyperresponsiveness, airway cellular composition was concomitantly investigated.

In order to investigate these effects, seven adult male cynomolgus monkeys (*Macaca fascicularis*, Charles River Primate Imports, Port Washington, N.Y.) weighing 4.67 to 8.2 kg were studied. All animals demonstrated a naturally occurring and reproducible respiratory sensitivity to inhaled *Ascaris suum* extract. Animals were studied anesthetized with ketamine hydrochloride (1 mg/kg, i.m.; Ketaset, Bristol Laboratories) and xylazine (4 mg/kg, i.m.; Rompun, Miles Laboratories, Inc.), intubated with a cuffed endotracheal tube (5.5 mm ID; Mallinckrodt Critical Care, cat ·86048) and seated in an upright position in a specially designed support chair. Ketamine (4 mg/kg, i.m.) was used alone to supplement anesthesia as needed.

Airway responsiveness (methacholine $PC_{100}$) followed by airway cell composition (BAL) were determined one day prior to and twenty hours after a single inhalation of Ascaris extract or three days prior to (Day 0) and three days after (Day 10) three alternate day (Days 3, 5 and 7) inhalations of Ascaris extract. All seven animals were studied in both protocols. A letter designation was assigned to each animal for presentation of results.

In asthmatics, the peak increase in airway responsiveness occurs three to twenty-four hours post allergen challenge (Cartier, A. et al., *J. Allergy Clin. Immunol.* 70:170-177 (1982), Cockcroft, D. W. et al., *Clinical Allergy* 7:503-513 (1977), Durham, S. R. et al., *J. Allergy Clin. Immunol.* 79:398-306 (1987)). Thus, airway responsiveness was measured twenty hours after the single inhalation of antigen.

However, to avoid anesthetizing each animal for a fourth time in a six day interval, airway responsiveness was not measured twenty hours after the multiple inhalation of antigen. Instead, airway responsiveness was measured three days after the multiple inhalations of antigen. It was discovered that airway inflammation (i.e. eosinophil infiltration) still persists three days after antigen inhalation (Wegner, C. D. et al., *Amer. Rev. Respir. Dis.* 135:A221 (1987) which reference is incorporated herein by reference).

*Ascaris suum* extract (Greer Laboratories, cat #B-33) was employed as antigen in the studies. The extract was diluted in phosphate buffered (5 mM, pH 7.4) saline (0.5%) (PBS), compressed air nebulized (Bird Micronebulizer, model 8158) and administered by intermittent positive pressure breathing (Bird Mark 7A Respirator) consisting of 30 inhalations to 20 cm $H_2O$ in approximately two minutes. For each animal, the previously determined concentration of Ascaris extract that caused a reproducible 150 to 300% acute increase in respiratory system resistance was used. Methacholine challenges were performed in an identical manner except that they consisted of only 15 breaths in one minute.

Respiratory system impedance (Zrs) was measured by discrete frequency (4–40 Hz in 11 equal logarithmic steps) sinusoidal forced oscillations superimposed on tidal breathing as described by Wegner, C. D. et al., (*Respir. Physiol.* 55:47–61 (1983) which reference is incorporated herein by reference). The means of the real or in-phase component of Zrs over the frequency range was then computed to provide a single value representation of respiratory system resistance (Rrs). Rrs was measured at 3, 7, 10, 15, 20 and 30 minutes after each antigen challenge and at 1 and 3 minutes after each methacholine challenge.

Airway Responsiveness was assessed by determining the concentration of nebulized and inhaled methacholine that induced a 100% increase in Rrs ($PC_{100}$). This was accomplished by administering increasing concentrations of methacholine (diluted with PBS) in half-logarithmic steps (at 7 minute intervals) until a greater than 100% increase in Rrs from baseline was obtained. The $PC_{100}$ was then calculated by linear regression analysis of the last two or three points on the logarithm methacholine concentration versus percent increase in Rrs plot.

Airway cell composition was assayed by bronchoalveolar lavage (BAL). A pediatric fiberoptic bronchoscope (Olympus Corporation, model BF-3C4) was guided past the carina until it wedged into typically a fifth to seventh generation bronchus. A single 15 ml aliquot of bicarbonate buffered (0.5 mM) normal saline (pH 7.4) was then infused and gently aspirated (return volume range from 7 to 10 ml) through a channel in the bronchoscope. Total leukocytes/ml of BAL was determined using a Coulter counter (Coulter Electronics, model $Z_{BI}$). Differential cell counts (a total of 200 cells counted) were performed on Wright-Geimsa strained cytocentrifuge (Shandon Cytospin, model 2) preparations. To prevent the effects of a prior BAL on subsequent BAL determinations, the BALs performed prior to and after antigen challenge were done on opposite sides of the lungs.

Analysis of variance was performed using the non-parametric Kruskal-Wallis Test (Chi-square approximation). Correlations were performed using Pearson product-moment and Spearman ranks of the variables. A p value of $>0.05$ was considered not significant.

Figures 8A, 8B:
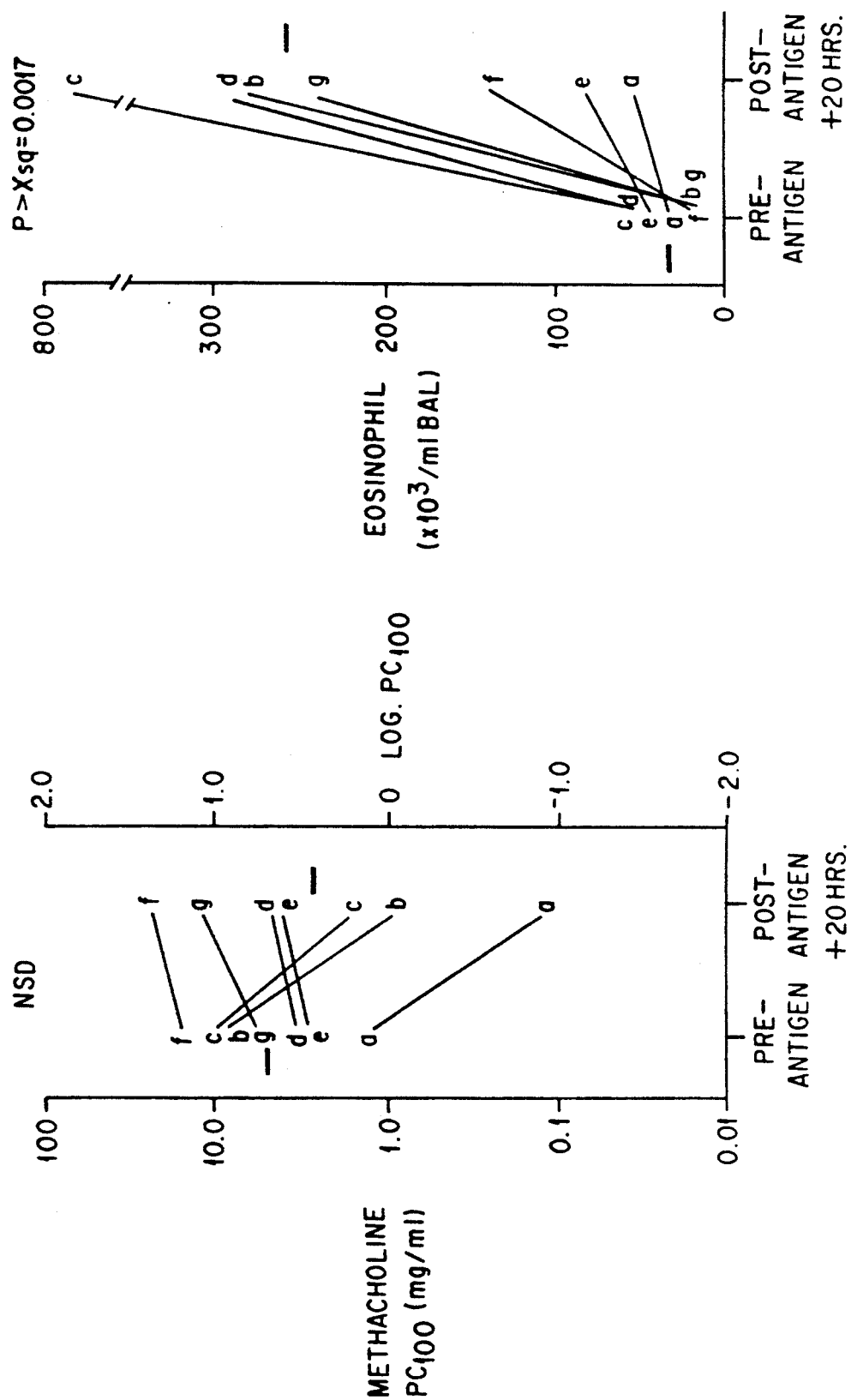
FIG. 8, panels a, b, c, d and e show changes induced by a single inhalation of antigen in (8A) inhaled methacholine $PC_{100}$, (8B) bronchoalveolar lavage (BAL) eosinophils, (8C) BAL neutrophils, (8D) BAL macrophages/monocytes, and (8E) BAL lymphocytes. Xsq=Kruskal-Wallis Test (Chi-square approximation). NSD=no significant difference. Each letter represents an individual monkey.

The single inhalation of antigen caused an acute increase in Rrs ($307\pm62\%$) that peaked 10–15 minutes post challenge, an increase in airway leukocytes ($267\pm19$ to $694\pm142\times10^3$/ml of BAL, $p>X^2=0.018$) and a decrease in methacholine $PC_{100}$ in 3 animals that was moderate ($>8$ fold) in two (FIG. 8A). The increase in airway leukocytes consisted of an infiltration of eosinophils in all animals (FIG. 8B), neutrophils in 3 animals (FIG. 8C), macrophages/monocytes in 5 animals (FIG. 8D) and lymphocytes in 4 animals (FIG. 8E). The magnitude and direction of the change in airway responsiveness (methacholine $PC_{100}$) did not correlate with the intensity of the acute increase in Rrs or with the magnitude/existence of the infiltration of any leukocyte subtype (Table 4).

Figures 9A, 9B:
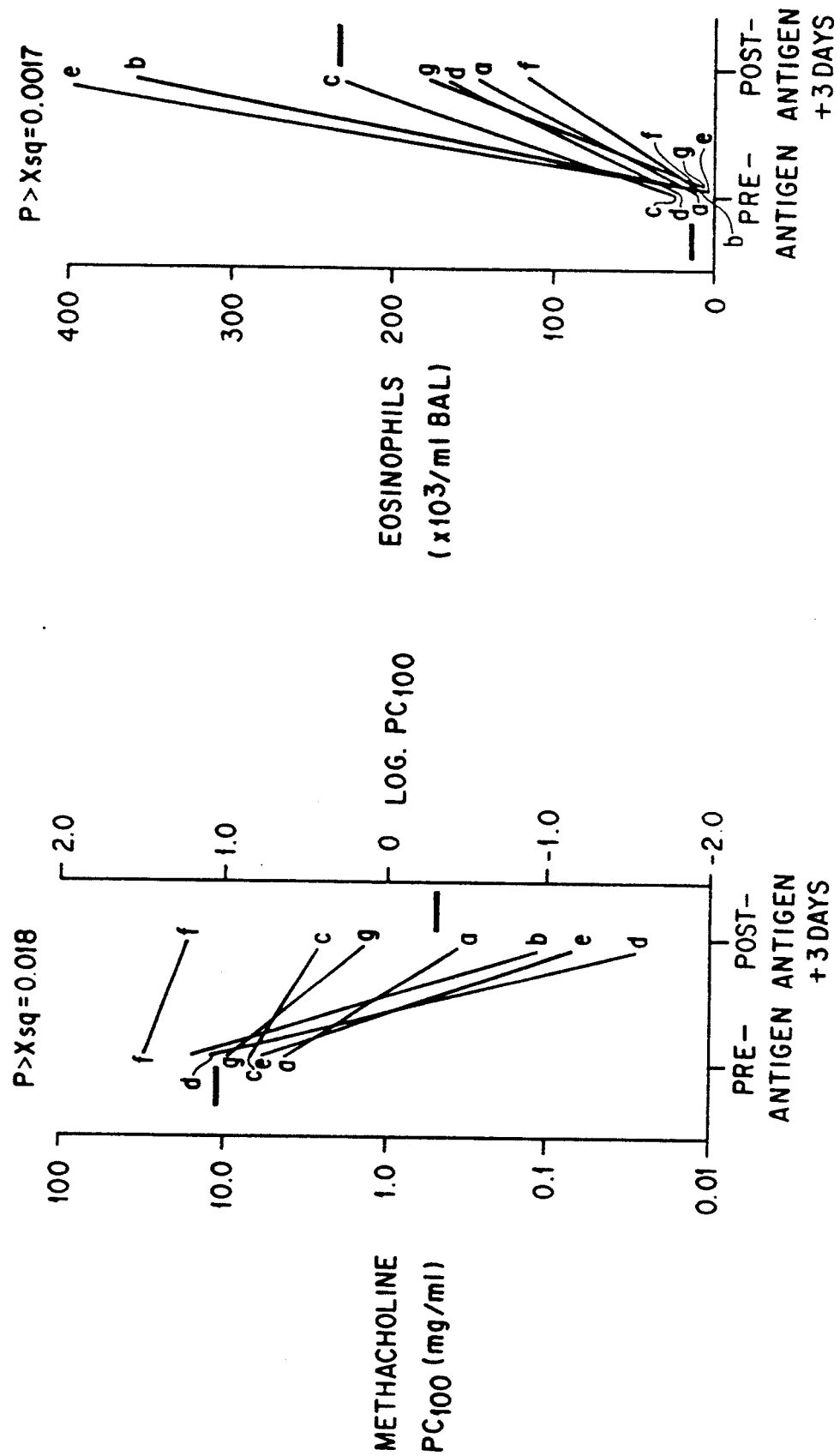
FIG. 9, panels a and b show changes induced by multiple inhalations of antigen in (9A) inhaled methachline $PC_{100}$ and (9B) bronchoalveolar lavage (BAL) eosinophils. Xsq=Kruskal-Wallis Test (Chi-square approximation). Each letter represents an individual monkey.

The multiple inhalations of antigen caused acute increases in Rrs ($178\pm48\%$, $380\pm83\%$ and $331\pm63\%$, respectively), and increase in airway leukocytes ($209\pm42$ to $553\pm128\times10^3$/ml of BAL, $p>X^2=0.0088$) and a decrease in methacholine $PC_{100}$ in all 7 animals that was moderate ($>8$ fold) in two and severe ($>80$ fold) in three (FIG. 9A). The increase in airway leukocytes consisted of a marked infiltration of eosinophils (FIG. 9B) and slight infiltration of neutrophils ($8.5\pm2.6$ to $31.0\pm7.5\times10^3$/ml of BAL, $p>X^2=0.010$). There was no significant infiltration of macrophages/monocytes ($179\pm36$ to $209\pm40\times10^3$/ml of BAL) or lymphocytes ($3.0\pm1.2$ to $3.0\pm1.3\times10^3$/ml of BAL). The magnitude of the increase in airway reactivity (decrease in $PC_{100}$) did not correlate with the intensity of the eosinophil infiltration or with the magnitude/direction of the change in airway reactivity ($PC_{100}$) induced by the single inhalation of antigen (Table 5).

TABLE 4

COMPARISON OF CHANGE IN METHACHOLINE $PC_{100}$ TO THE BRONCHOCONSTRICTION AND LEUKOCYTE INFILTRATION INDUCED BY A SINGLE INHALATION OF ANTIGEN*

| Animal | Change in Log. $PC_{100}$ | Increase in Rrs (%) | Leukocyte Infiltration ($\times 10^3$/ml BAL) | | | |
|---|---|---|---|---|---|---|
| | | | Eosin. | Neut. | Mac./Mono. | Lympho. |
| a | −1.02 | 494 | 23 | 297 | 105 | 3.3 |
| b | −0.95 | 278 | 266 | −33 | 421 | 20.5 |
| c | −0.75 | 181 | 668 | 87 | 104 | 2.7 |
| d | 0.16 | 244 | 242 | 6 | 253 | 18.6 |
| e | 0.21 | 525 | 38 | −6 | −73 | −1.6 |
| f | 0.24 | 66 | 124 | −2 | −78 | −3.0 |
| g | 0.36 | 360 | 221 | 178 | 264 | −0.4 |
| Mean | −0.25 | 307 | 226 | 76 | 142 | 5.8 |
| S.E. | ±0.24 | ±63 | ±82 | ±46 | ±69 | ±3.7 |

Definition of abbreviations: Log. - logarithm base 10; $PC_{100}$ - provocative concentration of methacholine required to cause a 100% increase in Rrs; Rrs - respiratory system resistance; BAL - bronchoalveolar lavage; Eosin. - eosinophils; Neut. - neutrophils; Mac./Mono. - macrophages/monocytes; Lympho. - lymphocytes.
*No significant correlations were found.

TABLE 5

COMPARISON OF CHANGE IN METHACHOLINE $PC_{100}$ TO EOSINOPHIL INFILTRATION INDUCED BY MULTIPLE INHALATIONS OF ANTIGEN TO THE CHANGE IN METHACHOLINE $PC_{100}$ INDUCED BY A SINGLE INHALATION OF ANTIGEN*

| Animal | Multiple Inhalations of Antigen | | Single Inhalation of Ag. |
|---|---|---|---|
| | Change in Log. $PC_{100}$ | Eosin. Infiltration ($\times 10^3$/ml BAL) | Change in Log. $PC_{100}$ |
| d | −2.66 | 144 | 0.16 |
| b | −2.13 | 352 | −0.95 |
| e | −1.95 | 409 | 0.21 |
| a | −1.07 | 135 | −1.02 |
| g | −0.97 | 174 | 0.36 |
| c | −0.43 | 206 | −0.75 |
| f | −0.27 | 109 | 0.24 |
| Mean | −1.36 | 218 | −0.25 |

TABLE 5-continued

COMPARISON OF CHANGE IN METHACHOLINE
$PC_{100}$ TO EOSINOPHIL INFILTRATION
INDUCED BY MULTIPLE INHALATIONS OF
ANTIGEN TO THE CHANGE IN METHACHOLINE
$PC_{100}$ INDUCED BY A SINGLE
INHALATION OF ANTIGEN*

| Animal | Multiple Inhalations of Antigen | | Single Inhalation of Ag. |
|---|---|---|---|
| | Change in Log. $PC_{100}$ | Eosin. Infiltration ($\times 10^3$/ml BAL) | Change in Log. $PC_{100}$ |
| S.E. | ±0.34 | ±44 | ±0.24 |

Definition of abbreviations: Log. - logarithm base 10; $PC_{100}$ - provocative concentration of methacholine required to cause a 100% increase in respiratory system resistance; BAL - bronchoalveolar lavage; Eosin. - eosinophils; Ag. - antigen.
*No significant correlations were found.

These experiments demonstrate that non-specific airway hyper-responsiveness, as assessed clinically by responsiveness of the airways to inhaled histamine, methacholine, exercise or cold air, is a characteristic feature of asthma (Boushey, H. A. et al., *Am. Rev. Respir. Dis.* 121:389–413 (1980), Hargrave, F. E. et al., *J. Allergy Clin. Immunol.* 68:347–355 (1981)). While the mechanisms underlying the pathogenesis of airway hyperresponsiveness are not known, results from many studies suggest that leukocyte infiltration (Gundel, R. H. et al., *Amer. Rev. Respir. Dis.* (1989), Marsh, W. R. et al., *Amer. Rev. Respir. Dis.* 131:875–879 (1985), Lazarus, S., *Amer. J. Med.* 81:2.14 7 (1986), O'Byrne, P. M., *Chest* 90:575–577 (1986), DeMonchy J. G. R. et al., *Amer. Rev. Respir. Dis.* 131:373–376 (1985), Wardlaw, A. J. et al. *Amer. Rev. Respir. Dis.* 137:62–69 (1988), Metzger, W. J. et al., *Chest* 89:477–483 (1986)) and/or mediators released by resident or infiltrating cells (Lanes, S. et al., *J. Appl. Physiol.* 61:864–872 (1986), Lazarus, S., *Amer. J. Med.* 81:2–7 (1986) O'Byrne, P. M., *Chest* 90:575–577 (1986), Wardlaw, A. J. et al., *Amer. Rev. Respir. Dis.* 137:62–69 (1988), Aizawa, Y. et al., *J. Appl. Physiol.* 59:1918–1923 (1985), O'Byrne, P. M. et al., *Prostaglandins* 4:537–543 (1984), Shulman, E. S., *Chest* 90:578–586 (1986)) are involved.

Antigen inhalation is known to induce an acute neutrophil and more chronic eosinophil airway infiltration (Wegner, C. D. et al., *Amer. Rev. Respir. Dis.* 135:A221 (1987)). A chronic idiopathic airway eosinophilia has been found to be associated with severe (>80 fold) airway hyperresponsiveness (Wegner, C. D. et al., *Amer. Rev. Respir. Dis.* 135:A222 (1987)). Multiple (four weekly) intratracheal instillations of antigen-coated beads have been found to induce marked increases in airway eosinophils and responsiveness (>8 fold) (Gundel, R. H. et al., *Amer. Rev. Respir. Dis.* (1989)). The experiments presented above provide a comparison of the effects of a single versus multiple (three alternate day) inhalations of *Ascaris suum* extract on airways responsiveness and leukocyte composition in "allergic" monkeys.

The single inhalation of antigen resulted in an acute broncho-constriction and, as measured 20 hours later, an infiltration of leukocytes (primarily and most consistently eosinophils) as well as an increase in airway responsiveness (decrease in inhaled methacholine $PC_{100}$) in 3 to 7 animals that was moderate (>8 fold) in two. These effects, as well as the frequency which they occurred, are similar to those reported for man. That is, in allergic asthmatics a single inhalation of antigen induces a predominantly eosinophilic leukocyte infiltration (DeMonchy, J. G. R. et al., *Amer. Rev. Respir. Dis.* 131:373–376 (1985)) and an increase (usually mild, >8 fold) in airway responsiveness in some individuals (Cartier, A. et al., *J. Allergy Clin. Immunol.* 70:170–177 (1982), Cockcroft, D. W. et al., *Clinical Allergy* 7:503–513 (1977)).

In contrast, the multiple inhalations of antigen induced, as assayed three days after the last challenge, an increase in airway responsiveness in all seven monkeys that was moderate (>8 fold) in two and sever (>80 fold) in three. These effects are also consistent with those reported for man. During the pollen season, the airway responsiveness of allergic asthmatics has been reported to increase in all individuals, although to varying degrees (Boulet, L.-P. et al., *J. Allergy. Clin. Immunol.* 71:399–406 (1983), Sotomayor, H. et al., *Amer. Rev. Respir. Dis.* 130:56–58 (1984)). Similarly, repeated exposure to occupational allergens has been shown to increase airway responsiveness in sensitive individuals (Chan-Yueng M., et al., *Amer. J. Med.* 72:411–415 (1982), Lam, S. et al., *J. Allergy Clin. Immunol.* 72:134–139 (1983), Lam, S. et al., *J. Allergy Clin. Immunol.* 63:28–34 (1979)).

In both the single and multiple inhalation of antigen protocols, the magnitude/direction of change in airway responsiveness did not correlate with the intensity of the leukocyte infiltration. This finding emphasizes the leukocyte infiltration alone is not enough to infer their direct involvement in the pathogenesis of airway hyperreactivity. Rather, the amount and type (simulator or inhibitor) of mediators released by the infiltrating and resident cells as well as the interactions occurring between the infiltrating and resident cells (e.g., eosinophils and airway epithelium) are important factors.

In summary, as has been previously reported for asthmatics, multltiple (but not single) inhalations of antigen induce a consistent (usually >8 fold) increase in airway responsiveness in monkeys. These findings indicate that this animal model can be used to screen for and identify agents capable of providing a therapy for asthma.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for reducing the severity of asthma in a patient which comprises providing to said patient an effective therapeutic amount of an agent selected from the group consisting of; (a) an isolated antibody which blocks leukocyte/ICAM-1 interactions by binding to ICAM-1, and (b) a fragment of said antibody (a), said fragment being capable of binding to ICAM-1.

2. The method of claim 1, wherein said antibody blocks the same leukocyte/ICAM-1 interaction as does the monoclonal antibody R6.5 produced by the hybridoma ATCC HB9580.

3. The method of claim 1 wherein said antibody is a monoclonal antibody.

4. The method of claim 3 wherein said monoclonal antibody is the monoclonal antibody R6.5 produced by hybridoma ATCC HB 9580.

* * * * *